US010585197B2

(12) United States Patent
Briden et al.

(10) Patent No.: US 10,585,197 B2
(45) Date of Patent: Mar. 10, 2020

(54) PORTABLE DETECTION APPARATUS AND METHOD

(71) Applicant: Atomic Energy Of Canada Limited, Chalk River (CA)

(72) Inventors: Neil Anthony Briden, Deep River (CA); Adrienne Lynn McKay Ethier, Petawawa (CA); Paul Kenyon Leeson, Deep River (CA); Joel Vandal, Deep River (CA)

(73) Assignee: Atomic Energy Of Canada Limited, Chalk River, Ontario (CA)

( * ) Notice: Subject to any disclaimer, the term of this patent is extended or adjusted under 35 U.S.C. 154(b) by 0 days.

(21) Appl. No.: 16/041,997

(22) Filed: Jul. 23, 2018

(65) Prior Publication Data

US 2018/0340896 A1 Nov. 29, 2018

Related U.S. Application Data

(63) Continuation of application No. 15/184,069, filed on Jun. 16, 2016, now Pat. No. 10,031,090.
(Continued)

(51) Int. Cl.
*G01T 1/36* (2006.01)
*G01T 3/00* (2006.01)
(Continued)

(52) U.S. Cl.
CPC ............... *G01T 1/36* (2013.01); *G01T 3/001* (2013.01); *B01D 29/0002* (2013.01); *G01N 23/2076* (2013.01)

(58) Field of Classification Search
None
See application file for complete search history.

(56) References Cited

U.S. PATENT DOCUMENTS 2,967,239 A 1/1961 Zemany
4,388,530 A 6/1983 Lubecki
(Continued)

OTHER PUBLICATIONS

Atomic Energy of Canada Limited, Innovative thinking to solve environmental challenges: TEAMS—Portable Mercury Analysis System, Voyageur Newsletter, Jun. 2012, vol. 7, Issue 6, Chalk River, Canada.
(Continued)

*Primary Examiner* — Yara B Green
(74) *Attorney, Agent, or Firm* — Kevin Shipley; Fogler, Rubinoff LLP

(57) ABSTRACT

A portable detection apparatus includes a fluid inlet to acquire a stream of fluid, a fluid outlet and a fluid flowpath therebetween. A pump circulates the fluid through the fluid flowpath. A gamma spectrometer and a mercury analyzer engage the fluid flowpath to analyze and detect radiation emitted by the fluid. A filter trap is in the fluid flowpath downstream from the gamma spectrometer and the mercury analyzer. The filter trap includes a valve assembly and at least a first and second filter for collecting gaseous constituents from the fluid. Each filter is removably connected to the first valve assembly. The valve assembly has a first configuration, in which the first filter is fluidly connected to the fluid flowpath and the second filter is fluidly isolated from the fluid flowpath, and a second configuration, in which the second filter is fluidly connected to the fluid flowpath and the first filter is fluidly isolated from the fluid flowpath.

18 Claims, 15 Drawing Sheets

Related U.S. Application Data

(60) Provisional application No. 62/180,325, filed on Jun. 16, 2015.

(51) Int. Cl.
*B01D 29/00* (2006.01)
*G01N 23/207* (2018.01)

(56) References Cited

U.S. PATENT DOCUMENTS

| | | | |
|---|---|---|---|
| 4,795,903 A | 1/1989 | Clayton | |
| 6,436,720 B1 * | 8/2002 | Oberbeck | B01J 19/0093 137/1 |
| 6,668,039 B2 | 12/2003 | Shepard | |
| 7,993,580 B2 | 8/2011 | Anderle | |
| 2008/0047370 A1 | 2/2008 | Vickery | |
| 2008/0156734 A1 * | 7/2008 | Burba | C02F 1/281 210/679 |
| 2008/0181473 A1 | 8/2008 | Garty et al. | |
| 2010/0285490 A1 | 11/2010 | Dees et al. | |
| 2015/0041408 A1 * | 2/2015 | Benavides | E21B 43/40 210/741 |

OTHER PUBLICATIONS

Atomic Energy of Canada Limited, The AECL Innovation Issue, Voyageur Newsletter, Sep. 2013, vol. 8, q Issue9, Chalk River, Canada.

Ethier et al, Evaluation of Mercury Atmospheric Releases from Medical Isotope Waste, 11th International Conference on Mercury as a Global Pollutant (11th ICMGP), 2012.

Ethier et al, Evaluation of Potential Mercury Releases From Medical Isotope Waste, Atomic Energy of Canada Limited Nuclear Review, Dec. 2013, vol. 2, Chalk River, Canada.

Holloway, A Literature Survey: Methods for the Removal of Iodine Species from Off-Gases and Liquid Waste Streams of Nuclear Power and Nuclear Fuel Reprocessing Plants, with Emphasis on Solid Sorbents, Oak Ridge National Laboratory, Jan. 1979, Tennessee, United States of America.

Burger, Technical Requirements for the Control of 129I in a Nuclear Fuels Reprocessing Plant, Pacific Northwest Laboratory, Nov. 1979, Washington, United States of America.

Boyer et al, Application of the Advanced Atmospheric Plume Profiler (APP) to Current Chalk River Laboratories Monitoring Systems, Canadian Nuclear Laboratories, vol. 4, No. 2, Dec. 2015, Chalk River, Canada.

Ethier et al, Evaluation of Potential Mercury Releases from Medical Isotope Waste, Canadian Nuclear Laboratories, vol. 2, No. 2, Dec. 2013, Chalk River, Canada.

* cited by examiner

PORTABLE DETECTION APPARATUS AND METHOD

CROSS-REFERENCE TO RELATED APPLICATIONS

This application is a continuation of U.S. patent application Ser. No. 15/184,069, filed Jun. 16, 2016 and entitled Portable Detection Apparatus and Method, which itself claims the benefit of 35 USC 119 based on the priority of US Provisional Patent Application 62/180,325, filed Jun. 16, 2015 and entitled Portable Detection Apparatus and Method. The entirety of these applications being incorporated herein in its entirety by reference.

FIELD

The present subject matter of the teachings described herein relates generally to a portable detection apparatus.

BACKGROUND

Environmental monitoring systems can be used in a number of circumstances. Accidents involving radiological cargo, unplanned discharges of contaminants to liquid or air, analysis of radiological storage systems, and remediation and decommission of contaminated buildings and areas all may involve analysis of the environment in and around a location of interest. With off-site laboratory analysis, it may take up to 6 weeks to ship acquired samples to a laboratory and receive results. In this time, conditions may shift leading to potential danger or further contamination. As well, if it turns out that the contamination is minimal or non-extant, significant and avoidable delays may be incurred.

In such cases, on-site analysis of environmental materials may be preferable. On-site analysis may minimize or prevent time delays in determining the potential dangers and environmental impact.

For example, mercuric (Hg) nitrate is used as a catalyst in the medical isotope production process to ensure consistent Mo-99 target dissolution. The subsequent high level radiological liquid waste is cemented into stainless steel pails and shipped to waste management areas for long term storage. The liquid waste may be stored in concrete tile holes. These tile holes are often engineered concrete structures surrounded by compacted soil and shielded with a concrete plug.

At current Mo-99 production rates, approximately 10 kg/yr of Hg in cemented waste is placed in storage. Structural degradation of Portland cement is often expected to occur in 7-20 years (after placement in tile hole), resulting in increased surface area and higher leaching rates. While the bulk of the stored Hg has been found to be strongly incorporated in the cement (~80%), there is potential for leaching of the Hg into the surrounding environment. As a result, it may be desirable to have a system to evaluate the potential for and magnitude of Hg releases during storage.

A portable detection apparatus may be desired to alleviate some of the above-noted concerns. As well, a compact and portable detection apparatus capable of analyzing and modelling a variety of contaminants released in fluid form may provide flexibility to monitor different environmental situations.

SUMMARY

This summary is intended to introduce the reader to the more detailed description that follows and not to limit or define any claimed or as yet unclaimed invention. One or more inventions may reside in any combination or subcombination of the elements or process steps disclosed in any part of this document including its claims and figures.

Environmental monitoring systems and apparatus can be used in a variety of situations to measure levels and emission levels of potential contaminants. To properly assess the environmental situation, detect emissions and profile the flow of emissions, it may be necessary to measure and analyze acquired fluid samples using a series or sequence of different techniques and analytical equipment. In some cases, analysis and monitoring equipment may be used at a site only once, for instance to investigate contamination or emissions from a recent unplanned emission such as caused by an accident, disaster or emergency. It may be beneficial in such circumstances to have a portable detection apparatus capable of performing the different measurements and analysis. A portable detection apparatus could provide relatively rapidly deployable monitoring and analysis capabilities to respond to emergencies. It may also be helpful for the detection apparatus to be modular in nature, to allow for modifications depending on the particular environmental assessments required.

In accordance with one broad aspect of the teachings disclosed herein, a portable detection apparatus may have an apparatus fluid inlet to draw in a stream of fluid, an apparatus fluid outlet and a fluid flowpath extending therebetween. The apparatus may also have a pump for circulating the fluid through the fluid flowpath and at least one of a gamma spectrometer, positioned to engage the fluid flowpath that is operable to detect radiation emitted by the fluid while the fluid is flowing through the fluid flowpath, and a mercury analyzer in the fluid flowpath operable to analyze the fluid flowing through the fluid flowpath. The apparatus may further include at least a first filter trap provided in the fluid flowpath downstream from the gamma spectrometer and the mercury analyzer. The first filter trap may have a first valve assembly and at least a first filter and a second filter for collecting gaseous constituents from the stream of fluid that are removably connected to the first valve assembly. The first valve assembly may be configurable in a first configuration in which the first filter is fluidly connected to the fluid flowpath and the second filter is fluidly isolated from the fluid flowpath, and a second configuration in which the second filter is fluidly connected to the fluid flowpath and the first filter is fluidly isolated from the fluid flowpath.

In some examples, the gamma spectrometer may be upstream from the mercury analyzer.

In some examples, the fluid flowpath may have a fluid conduit with a conduit inlet and a conduit outlet downstream from the conduit inlet, and the gamma spectrometer and the mercury analyzer may be between the conduit inlet and the conduit outlet and the first filter trap may between the conduit outlet and the apparatus fluid outlet. In some particular examples, the gamma spectrometer may have a first sample channel that is sized to removably receive a portion of the fluid conduit, and the gamma spectrometer may be operable to detect ionizing radiation emitted by the fluid while the fluid is flowing through the first sample channel.

In some examples, the apparatus may also have a radiation shield at least partially covering the gamma spectrometer and the sample channel to shield the portion of the fluid conduit received within the sample channel from background radiation.

In some examples, the gamma spectrometer may have a second sample channel that is a different size than the first sample channel and is configured to receive a portion of a second fluid conduit that has a different size than the fluid conduit (i.e. the primary fluid conduit).

In some examples, the apparatus may also have a meteorological station that includes at least one of a temperature sensor, a pressure sensor, rain sensor and a wind speed sensor.

In some examples, the apparatus may also have a primary housing containing the gamma spectrometer and the mercury analyzer, and a filter housing that is external the primary housing and contains the first filter trap.

In some examples, the apparatus fluid inlet may be external and spaced apart from the primary housing. In some particular examples, the apparatus fluid inlet may be spaced apart from the primary housing by a distance of between about 1 m and 30 m.

In some examples, the primary housing may include the apparatus fluid inlet and the filter housing may include the apparatus fluid outlet.

In some examples, the primary housing may include a primary housing fluid outlet and the filter housing may include a filter housing fluid inlet that is detachably fluidly connectable to the primary housing fluid outlet by a fluid coupling. In some particular examples, the filter housing may be detachably mounted to the primary housing and when the filter housing fluid inlet is detached from the primary housing fluid outlet the filter housing may be detachable from the primary housing. In some particular examples, the primary housing may have a door that is movable between a closed position, in which the primary housing is fluidly sealed with the exception of the apparatus fluid inlet and the primary housing fluid outlet, and an open position, in which at least one of the gamma spectrometer and the mercury analyzer are accessible.

In some examples, the filter housing may have a body and lid that is movable between a closed position and an open position, and the first and second filters may be removable when the lid is in the open position.

In some examples, the first valve assembly may have a first manifold with a first manifold inlet connectable in fluid communication with the filter housing fluid inlet, a first manifold outlet with a first valve and a second manifold outlet with a second valve, and the first filter may be connectable to the first manifold outlet and the second filter may be connectable to the second manifold outlet. In some particular examples, the first valve and second valve may be operable independently of each other.

In some examples, the apparatus may further include a controller configured to receive inputs from the gamma spectrometer and mercury analyzer. In some particular examples, the controller may be configured to generate at least one of plume concentration data and a plume profile map based on the received inputs.

In some examples, the apparatus may have at least two wheels rollingly supporting the portable detection apparatus and a coupling for connecting the portable detection apparatus to a vehicle.

In some examples, the apparatus may have a second filter trap in the fluid flowpath downstream from the gamma spectrometer and the mercury analyzer. The second filter trap may include a second valve assembly and at least a third filter and a fourth filter configured for collecting gaseous constituents from the stream of fluid and removably connected to the second valve assembly. The second valve assembly may be configurable in a first configuration in which the third filter is fluidly connected to the fluid flowpath and the fourth filter is fluidly isolated from the fluid flowpath, and a second configuration in which the fourth filter is fluidly connected to the fluid flowpath and the third filter is fluidly isolated from the fluid flowpath. In some particular examples, the second filter trap may be fluidly connected in series downstream from the first filter trap.

In some particular examples, the apparatus may have a primary housing containing the gamma spectrometer and the mercury analyzer, a first filter housing containing the first filter trap and a second filter housing containing the second filter trap, and the first filter housing and second filter housing may be external the primary housing and may be detachably mounted to the primary housing. In some particular examples, the second filter trap may be fluidly connected in parallel with the first filter trap whereby one of the first filter housing and the second filter housing can be detached from the primary housing without interrupting the fluid communication between the other of the first filter housing and the second filter housing and the primary housing.

In some examples, the apparatus may have at least one on board power source electrically connected to at least one of the gamma spectrometer, mercury analyzer and filter trap.

In some examples, the portable detection apparatus may have a width in a first direction and a length in a second direction that is orthogonal to the first direction, and the width and length may each be less than about 5 feet. In some particular examples, the width may be less than about 5 feet and the length may be less than about 3 feet.

In some examples, the apparatus may have a particle filter covering the apparatus fluid inlet to filter particulate from the fluid as it enters the fluid flowpath.

In some examples, the pump may be integral with the mercury analyzer.

In accordance with another broad aspect of the teachings described herein, which may be used alone or in combination with any other aspects, a portable detection apparatus may have a sample line configured to receive a flowing fluid and a detector positioned to detect ionizing radiation emitted by the fluid flowing through the sample line. The apparatus may also have a controller linked to the detector that is operable to trigger the detector at a predetermined sampling rate while the fluid is flowing through the sample line and a radiation shield at least partially surrounding the sample line and the detector to shield the detector from background radiation. In some particular examples, the detector may be a gamma spectrometer.

In accordance with another broad aspect of the teachings described herein, which may be used alone or in combination with any other aspects, a method of monitoring fluid contaminations may include drawing a stream of the fluid into a fluid flowpath and analyzing the flowing fluid using at least one flow-through detection apparatus. The method may also include capturing a first batch of particulates from the fluid by directing at least a portion of the fluid exiting the flow-through detection apparatus to flow through a first filter, isolating the first filter from the fluid flowpath, and capturing a second batch of particulates from the fluid by directing the at least a portion of the fluid exiting the flow-through detection apparatus to flow through a second filter. In some particular examples, analyzing the flowing fluid may include at least one of detecting radiation and collecting mercury from the flowing fluid.

Other aspects and features of the teachings disclosed herein will become apparent, to those ordinarily skilled in the art, upon review of the following description of the specific examples of the present disclosure.

DRAWINGS

The drawings included herewith are for illustrating various examples of articles, methods, and apparatuses of the teaching of the present specification and are not intended to limit the scope of what is taught in any way.

DETAILED DESCRIPTION

Figure 1A:
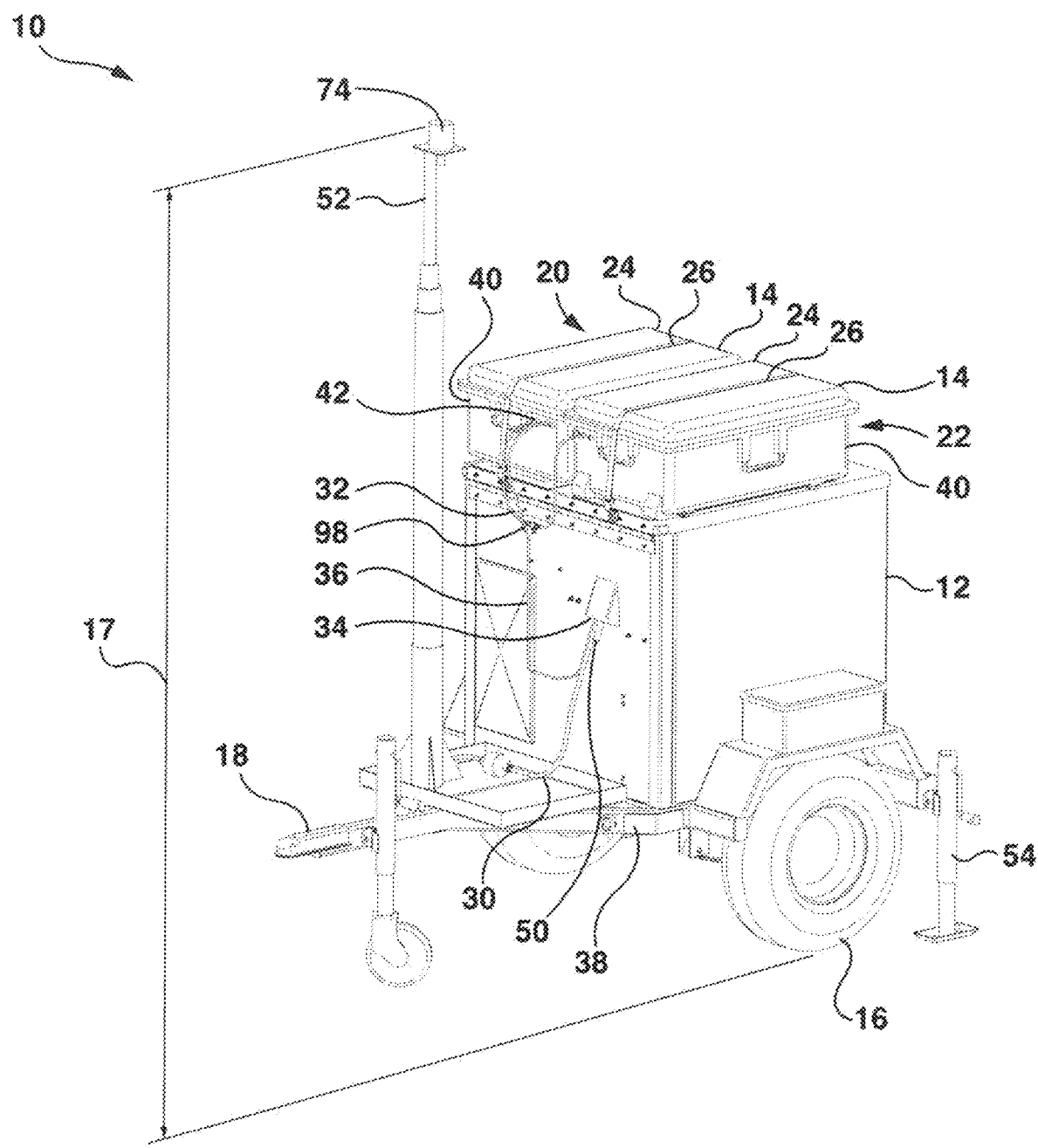
FIG. 1A is a perspective view of one example of a portable detection apparatus.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Emergency response situations involving unplanned releases of radiological material may require monitoring or analysis. Such situations include road accidents involving radiological cargo and unplanned discharges to liquid or air. Environmental remediation and decommissioning is another example of a situation where environmental monitoring systems may be employed.

Analysis of environmental materials may involve an up to 6 week turnaround time to ship samples to an off-site laboratory and receive results. On-site analysis and monitoring of contaminants in air, dose and contaminant dispersion may all be helpful in the aftermath of an unplanned release of radiological material. On-site analysis of the gamma radiation levels of different environmental materials such as soil, sediment, water, vegetation may avoid time delays and costs by determining if material is contaminated. If material is uncontaminated and/or below acceptable limits, it can be put back in place, also avoiding cost of disposition of waste. If material is contaminated, it can then be shipped to a laboratory for further analysis if desired. Furthermore, continuous monitoring of particulate, gases in air, and/or liquids may be desirable during remediation and decommissioning of contaminated buildings or areas. To help facilitate measurement and monitoring of fluid contaminations in a target location the inventors have developed a portable detection apparatus.

Optionally, the detection apparatus may include a sample line or fluid inlet to draw in or receive a flowing fluid, such as air or water. The detection apparatus may include one or more detectors positioned to analyze the fluid, including, for example, when the flowing through the sample line. Optionally, the detectors may include flow-through type detectors that are capable of analyzing the fluid in real time, i.e. as it flows through the sample line. Optionally, the detectors can also be configured to output data in real time, or may be configured to collect and store the data locally and only output the data at pre-determine intervals and/or when queried by a user, controller or other part of the detection apparatus. Alternatively, or in addition to the flow-through type detectors, the detection apparatus may include at least one off-line or static type detector that is configured to analyze a static, non-flowing fluid.

The detectors may be any detector that is suitable for detecting targeted contaminant in a particular environment. For example, if radioactive materials are expected to be present in the sampling environment, the detection apparatus may include a radiation detector such as, for example, a gamma spectrometer. If mercury is expected to be present, the detection apparatus may also include a mercury analyzer. Optionally, some or all of the detectors may be modular and may be removably connected to the detection apparatus. This may allow different combinations of detectors to be selected based on the environment in which the detection apparatus is to be deployed, and/or to target specific contaminants.

Optionally, the detection apparatus may also include one or more filter traps for collecting particles and/or gaseous constituents from the acquired stream of fluid. Preferably, the filter traps are placed downstream of the flow-through detectors so as not to compromise the measurements from those detectors, for example by filtering out the particles and/or gaseous constituents that are to be detected by the detectors. Each filter trap may include a plurality of individual filters that may optionally be removably connected to a valve assembly. The valve assembly can have a number of different configurations and may be used to regulate the flow of the fluid and to direct the stream of fluid through the filters. Optionally, the valve assembly can be configured to route the fluid stream through on filter at a time. Alternatively, the valve assembly may be operable to divide the fluid stream between two or more filters in parallel. The filter traps need not be configured to provide real time analysis. Instead, using the valve assembly, the fluid may be routed through a given filter for a pre-determined period of time.

The filter can then be analyzed off-line, and optionally removed from the detection apparatus and analyzed in a remote location such as a laboratory. Optionally, the data from the filters can be co-related with the data from the flow-through detectors. For example, data from the flow-through detectors from a specific period of time can be associated with the contents of one or more filters that were receiving the fluid flow during the same time period.

The portable detection apparatus may also include other associated monitoring sensors and equipment, including, for example combustible gas monitors (suitable for monitoring $CH_4$, $CO_2$, CO, $H_4S$, $SO_2$, NO, $H_2$, $O_2$); high volume air samplers (operable to collect data on total suspended particulates in air—optionally both total and active particles) Ultra Violet radiation light sensors (UVA/UVC radiation light sensors); does rate meters and detectors; flow meters; flux chambers; wireless temperature, humidity, and barometric pressure probes; rain gauges (optionally an optical rain gauge); a meteorological tower; and sampling chambers to conduct radiological measurements on other environmental media (e.g. vegetation, soil, sediment, water).

The portable detection apparatus may also include one or more controllers for controlling the operation of the various detectors, filter traps and other equipment, and/or for collecting an processing the data collected. Optionally, the controllers may include one or more processors, a storage module, a communication module (including a receiver and a transmitter), a user output device and any other suitable components. The controller may interface with the detectors and filters to adjust calibration and operational parameters, as well as to receive measurement and analysis data. Optionally, the controller may be provided with software to enable the controller to generate an fluid dispersion model, for example, in the form of a plume profile, to model how fluid contaminants have dispersed within the surrounding environment and/or predict the future dispersion of the contaminants, based on the detected contaminant concentrations, and properties and the current and past meteorological conditions.

Optionally, the meteorological tower or weather station, and any of the other equipment provided on the detection apparatus, can also supply data to the controller that can be used in the generation of the plume profile model. The controller may also be configured to receive data from remote sources (such as a network storage device, meteorological data from other locations, facility monitoring devices, other environmental sensors, etc.) and use this data to help generate the plume model. The model may generate an estimate of emission rate for a contaminant source, and optionally may then provide a map of concentrations and doses over a given area from a known or suspected contaminant source. The model may be used to locate the most effective locations to sample, as well as to infer the location of an emission source given the location of sample uptake and the wind speed. For example, the behavior of mercury contaminant released into the air tends to be influenced by temperature and solar radiation. To help improve the accuracy of the mercury dispersion model the portable detection apparatus may include probes to continuously measure temperature, pressure and humidity and provide the data to the controller (optionally wirelessly, for example using remote sensors that are up to 90 m away from the detection apparatus) as well as a UVA/UVC meter. A precipitation sensor, such as an optical rain gauge, may also be used to estimate precipitation levels and/or wet and dry deposition and provide this data to the controller.

Figure 1B:
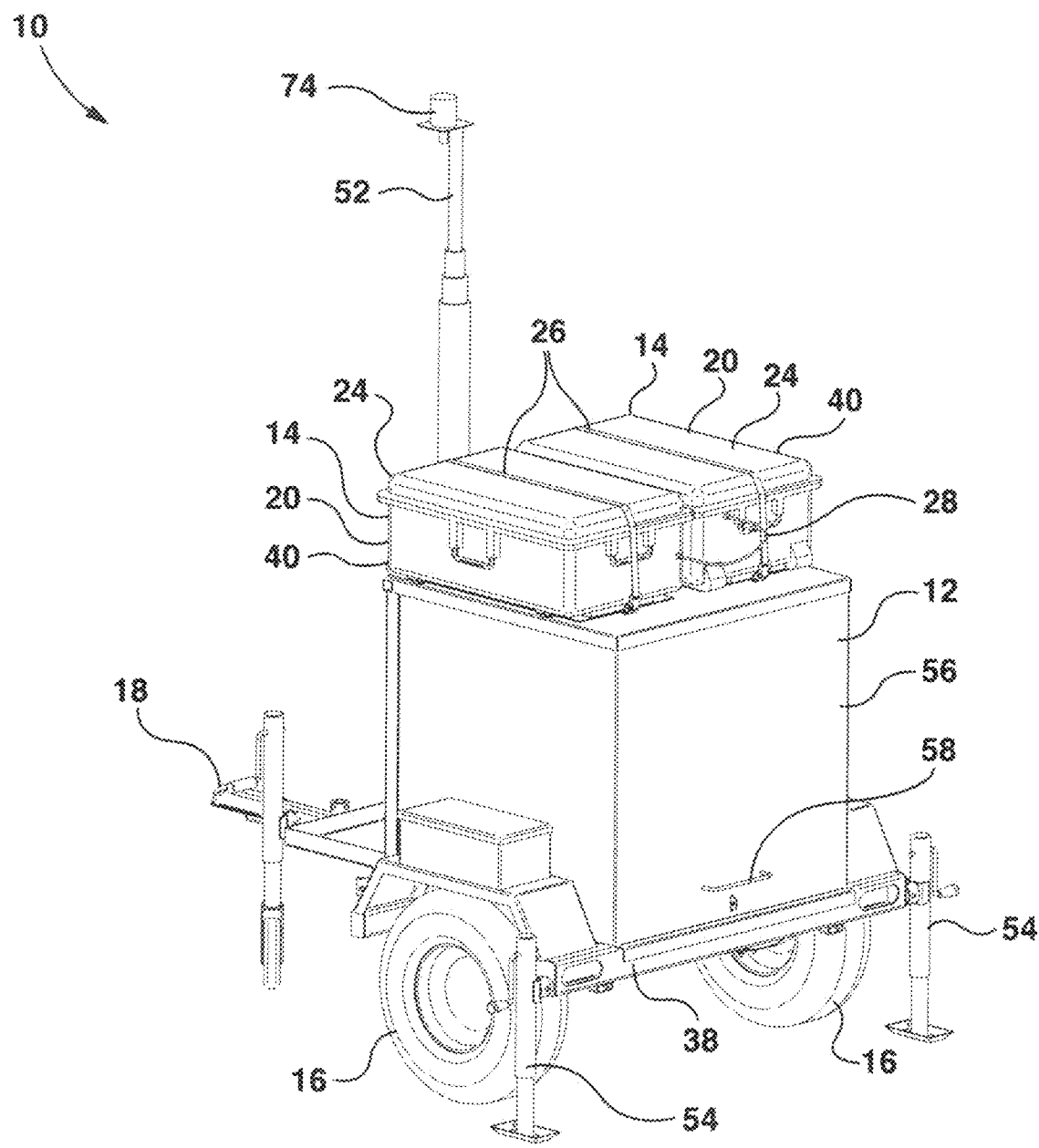
FIG. 1B is another perspective view of one example of the portable detection apparatus of FIG. 1.

Reference will now be made to FIGS. 1A and 1B. FIG. 1A shows a perspective view of a portable detection apparatus 10 from the top, front and left hand side. FIG. 1B shows a perspective view of portable detection apparatus 10 from the top, back and left hand side. In the illustrated example, the portable detection apparatus 10 is configured as a portable trailer that can be transported to a variety of different analysis/detection locations, for example by pulling the trailer with a vehicle or by maneuvering the trailer by hand.

In the illustrated example, the portable detection apparatus 10 can be used to monitor and analyze fluid contaminations and emissions in the surrounding environment by drawing a portion of the surrounding air into the apparatus 10 for analysis. Specifically, the apparatus 10 includes an apparatus fluid inlet 30 used to draw in a stream of fluid and an apparatus fluid outlet 32. The stream of fluid may be received by, and flow through, a sample line or fluid flowpath. In some examples, a particle filter may cover the apparatus fluid inlet 30 to help filter unwanted particulate from the fluid as it enters the fluid flowpath. This may help reduce fouling of the detectors and other equipment in communication with the fluid flow path.

The portable detection apparatus 10 also includes an apparatus fluid outlet that is preferably downstream from the detectors, filters and other sampling equipment, and is fluidly connected to the fluid inlet 30 via the fluid flowpath. Optionally, one or more flow-through detectors may be positioned along the sample line or fluid flowpath to analyze the acquired stream of fluid. For instance, the flow-through detectors may include at least one of a gamma spectrometer and a mercury analyzer. In the present example the inventors have adapted a FALCON® 5000 gamma spectrometer manufactured by Canberra Industries Inc to operate as a flow-through gamma spectrometer that is suitable for use in the portable detection apparatus 10. Specifically, the FALCON® 5000 is modified from its standard specifications by modifying the gamma spectrometry software to allow for repeated measurements over a pre-determined time period while the fluid flows past the detector. One example of a suitable mercury analyzer is the TEKRAN® 2537B Continuous Hg Vapour Analyzer, manufactured by Tekran Instruments Corporation.

The flow-through detectors (i.e. gamma spectrometer, mercury analyzer and other detectors) may be contained within primary housing 12. The flow-through detectors may be configured to receive the fluid directly (i.e. be in direct contact with the fluid as part of the air flow path), or alternatively may be configured to analyze the fluid while it remains within the sample line (such as by observing and/or sensing the fluid through the sidewalls of the sampling line).

Optionally, the portable detection apparatus 10 may include a single outer shell or housing that contains the detectors, filters and other equipment. The housing may be configured to be generally weather-resistant to help protect the internal equipment from rain, snow, wind and other environmental factors. Optionally, the housing may be sealed so that it is substantially water-tight and/or substantially air-tight, with the exception of the fluid inlet and outlets (and other instrumentation ports and/or access points as required). The housing may also be configured to help secure the equipment and protect it from tampering and/or theft. For example, the housing may be made from a relatively strong material, such as metal or plastic, and may include a locking mechanism or other apparatus to help prevent unauthorized access into the interior of the portable detection apparatus. This may help protect the equipment if the portable detection apparatus is left unattended in a monitoring location.

Alternatively, instead of a single housing or outer shell, the portable detection apparatus may include two or more housings, each containing some of the equipment. Providing separating housings may allow the properties of each housing to be tailored to its function and/or to the equipment within the housing. For example, one housing may be made from metal while another is made from plastic. Optionally, the housings may be individually sealed so that the interior of one housing is generally isolated from the interior of another housing. This may help reduce the chances of cross-contamination between the housings. For example, if there is a fluid leak within the interior of one housing, the equipment in a separate, isolated housing may not be affected. Providing separate housings may also help facilitate the modular aspect of the portable detection apparatus design, as individual housings may be added or removed from the apparatus to modify its scale and/or capabilities. Some of the housings may be detachably connected to each other. For example, a housing containing the filter trap equipment may be detachable from a housing that contains the flow-through detectors. This may allow the filter traps to be removed or replaced (for example to take the filters to a testing location) without disturbing the flow-through detectors. Optionally, some or all of the housings may be radioactively shielded. This may help protect some equipment, such as the controller, from radiation that is present in other portions of the portable detection apparatus, such as proximate the gamma spectrometer or filters.

Referring to FIGS. 1A and 1B, in the illustrated example the portable detection apparatus 10 includes primary housing 12 and two separate filter housings 14 that are external and isolated from the primary housing 12 (a different number of filter housings may be used on different embodiments of a detection apparatus). Filter housings 14 are provided in the form of separate, brief-case type enclosures that are detachably secured to primary housing 12. In the illustrated example, a detachable filter housing attachment member in the form of an adjustable strap 26 is used to detachably secure the filter housings 14 to the primary housing 12. When filter housing 14 is in place on top of primary housing 12, the strap 26 can be attached to anchors on the top or sides of primary housing 12. The strap 26 can then be tightened to secure filter housing 14 to primary housing 12. Additional attachment mechanisms may also be used, such as guides on the surface of primary housing 12 to prevent lateral displacement of filter housing 14. Providing a releasable strap 26 may allow each filter housing 14 to be separated from the primary housing 12 and replaced with replacement filter housing. This may help facilitate quick changes of the filter strap equipment, wherein a user can quickly swap a new filter housing 14 for a used filter housing 14 without having to individually deal with all of the internal filters, etc. Providing a quick change mechanism may help reduce the amount of time a user needs to spend in the field with the portable detection apparatus 10, which may be beneficial if the area is unpleasant or dangerous (i.e. radioactively contaminated, cold, hot, etc.).

Filter housings 14 may each contain at least one first trap. In some cases, a first filter trap 20 and a second filter trap 22 may be used. The filter traps can be used to trap contaminants contained with the acquired stream of fluid. The filter traps are positioned downstream of the flow-through detectors so that analysis of the fluid by the flow-through detectors is not adversely affected when contaminants are removed from the fluid by the filter traps.

Figure 6A:
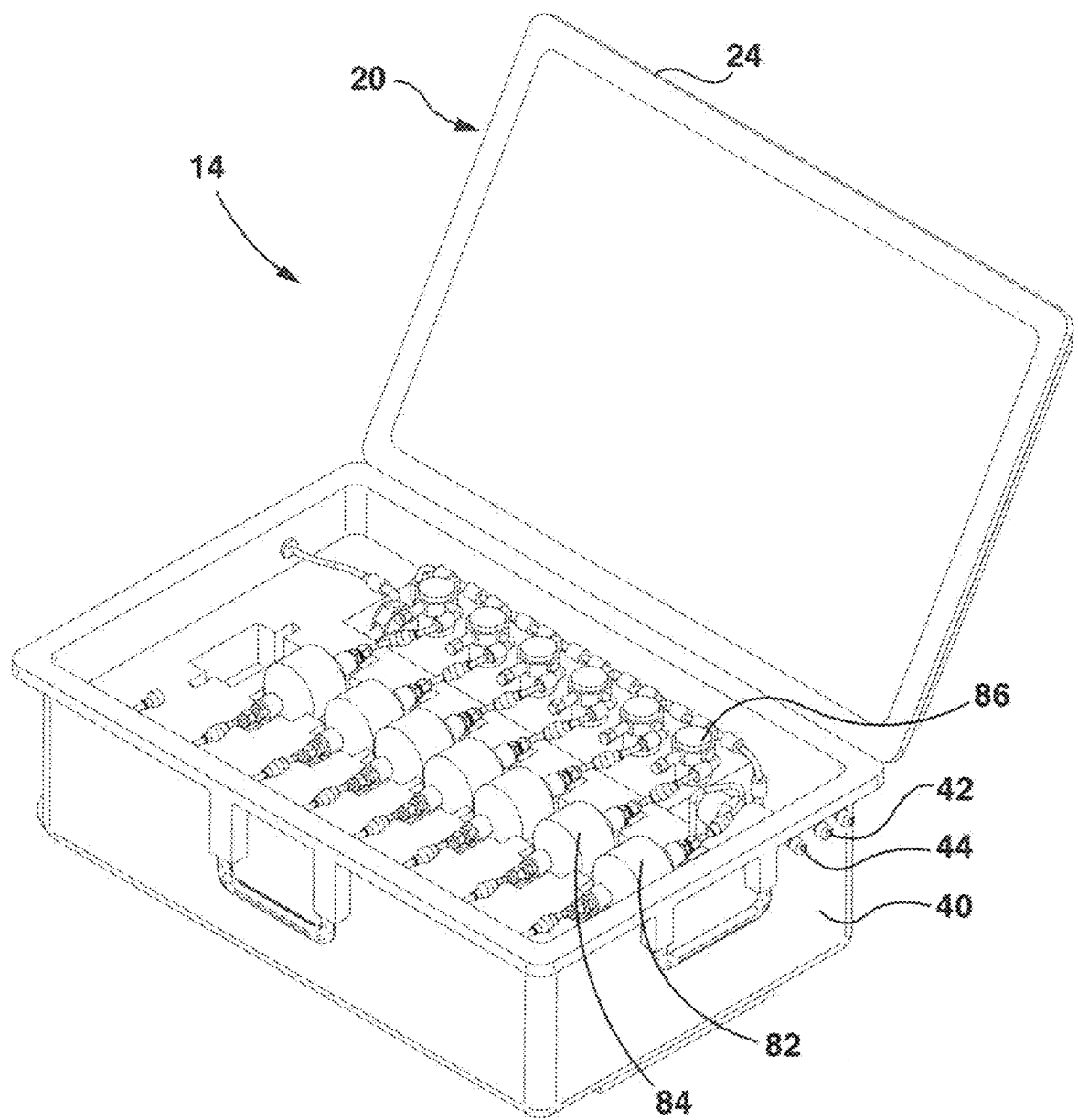
FIG. 6A is a perspective view of one example of a filter trap for a portable detection apparatus with the lid open.

Referring to FIG. 6A, each filter housing 14 has a housing body 40 and a lid 24. Lid 24 can transition between an open position and a closed position. In the open position, access is provided to filter traps 20 and 22 and the filters 82 and 84 therein can be removable. In the closed position, the lid 24 and housing body 40 can provide a waterproof seal, to prevent contamination of filter traps 20 and 22. Optionally, the lid 24 (or other portion of the filter housing 14) may be transparent. This may allow a user to inspect the interior of the filter housing 14 without having to open the lid 24.

In the illustrated example, the filter housings 14 can be rugged waterproof cases that lie on top of primary housing 12 and have exterior dimensions of about 79.5 cm×51.8 cm×31.0 cm. There may also be additional shielding material on top of the primary housing 12 or incorporated into the filter housing 14. This may be useful if the filters are expected to capture radioactive materials.

The shielding material may be any suitable material, including tungsten-impregnated, silicone pieces such as Tungsten Siflex. In some cases, the additional shielding material may be about ⅛" thick. The shielding effectiveness of the additional shielding material may be about 21% for Cs-137 and about 12% for Co-60. The half-value layer (HVL) of the additional shielding material may be about 0.92 cm (0.36") for Cs-137 while for Co-60 the HVL may be about 1.60 cm (0.63").

Referring again to FIGS. 1A and 1B, the fluid inlet 30 may be contained within primary housing 12. Alternatively, apparatus fluid inlet 30 may be external and spaced apart from primary housing 12. For instance, apparatus fluid inlet 30 may be spaced apart from primary housing 12 by a distance of between about 1 m and 30 m or more. This may allow the fluid inlet location to be spaced apart from the primary housing 12. This may allow a stream of fluid to be acquired from a position closer to a target source while placing the apparatus 10 farther from the source to reduce the likelihood of contamination. This may also allow the fluid inlet 30 to be directly connected to fluid source, such as a pipe, smoke stack, existing fluid monitoring systems and other apparatuses.

Preferably, the fluid inlet 30 is fluidly coupled to a fluid hose or conduit that forms the sampling line carrying the acquired stream of fluid to through primary housing 12, and the detectors housed therein. The sampling line may be rigid or flexible (or both in different regions) and may be of any suitable diameter.

Apparatus fluid outlet 32 may allow the stream of fluid to be released after passing through the flow-through detectors and filter traps. In some cases, apparatus fluid outlet 32 may be contained within the filter housing 14. Apparatus fluid outlet 32 may be coupled to a fluid hose or conduit that releases the stream of fluid downwind and/or downstream of the target source to reduce the risk of contamination of the apparatus 10.

Figure 2A:
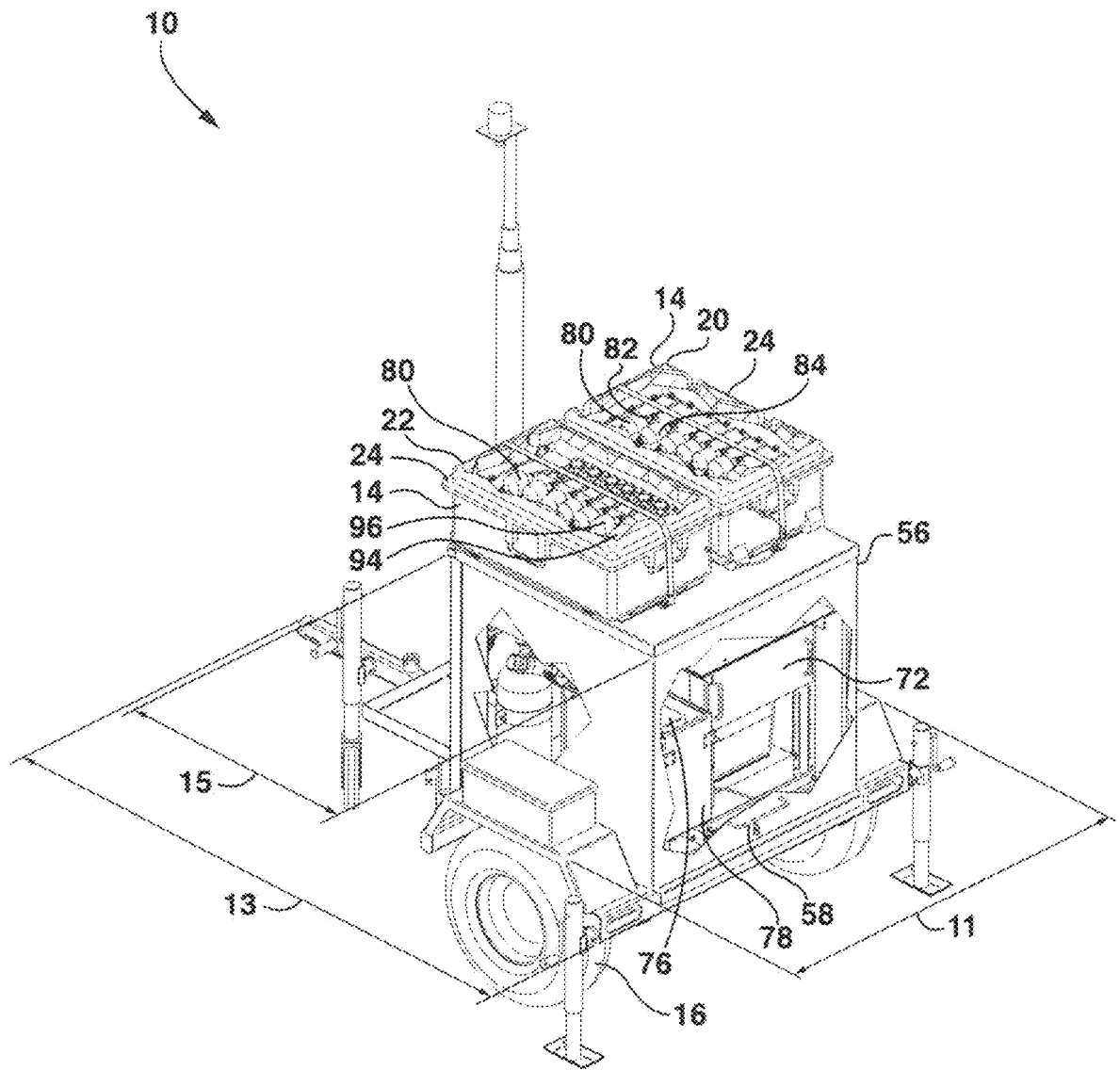
FIG. 2A is another perspective view of one example of the portable detection apparatus of FIG. 1.
Figure 2B:
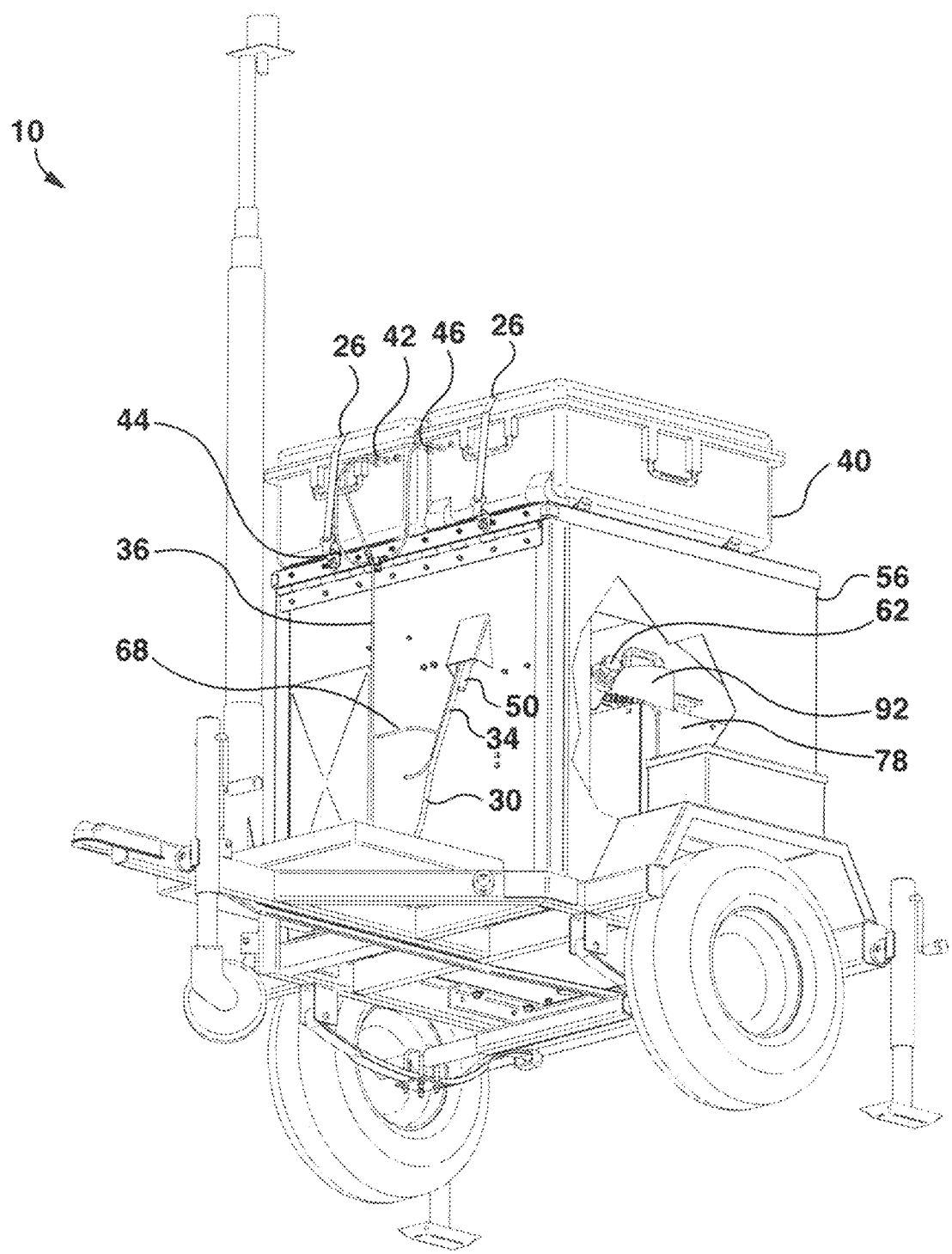
FIG. 2B is a further perspective view of one example of the portable detection apparatus of FIG. 1.
Figure 5:
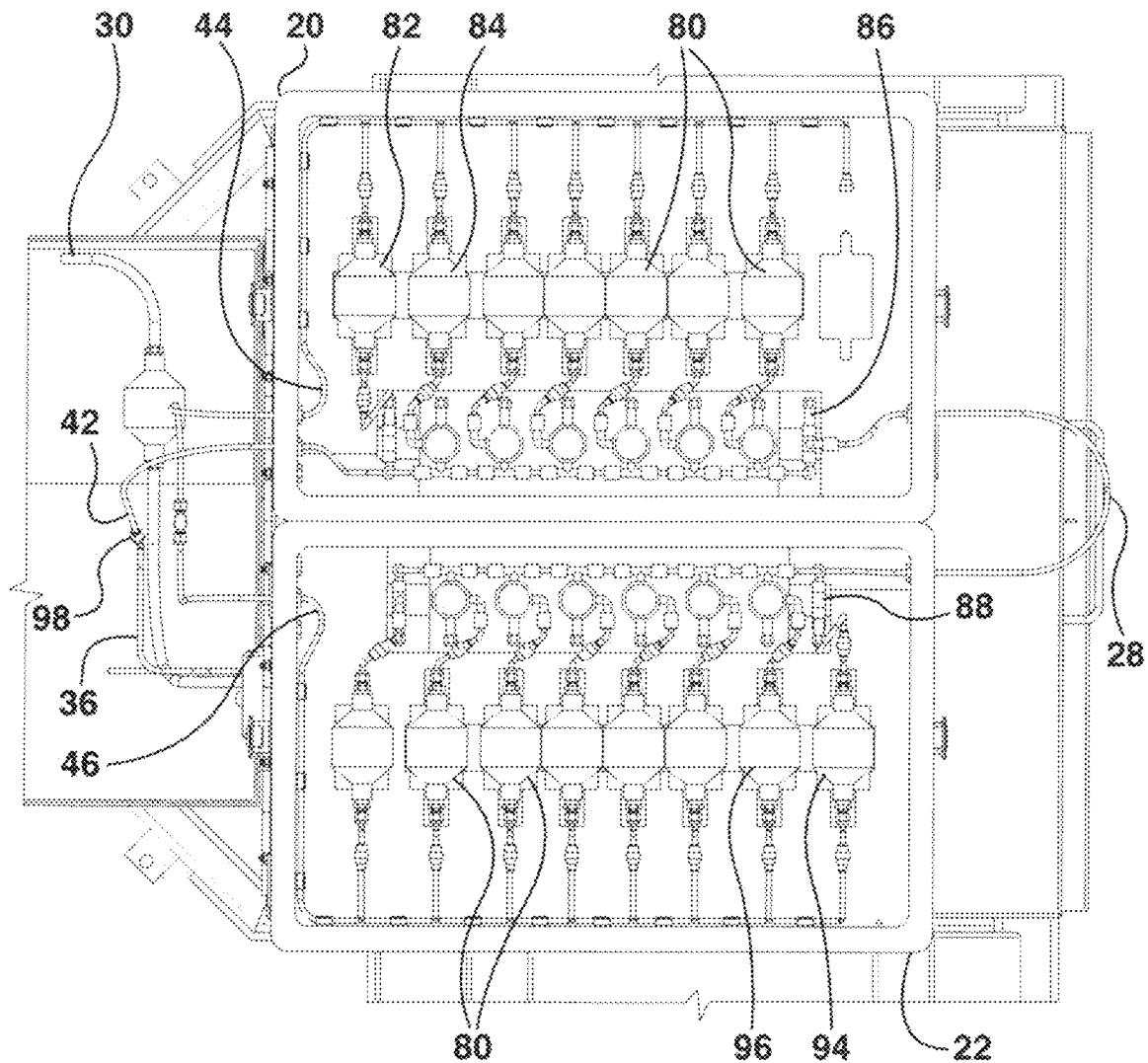
FIG. 5 is a top view of one example of the portable detection apparatus of FIG. 1 with the lid of the filter housing removed.

Referring to FIGS. 2B and 5, in the illustrated example the sampling line is providing in the form of a flexible hose that has a conduit inlet 34 and a conduit outlet 36 downstream from conduit inlet 34. The flow-through detectors such as the gamma spectrometer and the mercury analyzer can be positioned between conduit inlet 34 and conduit outlet 36. Filter traps 20 and 22 may be positioned after the conduit outlet 36, and between conduit outlet 36 and apparatus fluid outlet 32.

When the flow-through detectors are contained with primary housing 12, conduit inlet 34 may also be referred to as a primary housing inlet and conduit outlet 36 may also be referred to as the primary housing outlet. The filter housing 14 may include a filter housing fluid inlet 42 that is detachably fluidly connectable to the primary housing fluid outlet 36 by fluid coupling 98 (FIG. 1A). This may allow the filter housing 14 to be detachable from primary housing 12, when the filter housing fluid inlet 42 is detached from primary housing fluid outlet 36 by detaching fluid coupling 98.

Detachably mounting filter housings 14 to primary housing 12 may allow filter housing 14, and thereby filter traps 20 and 22 to be removed for purposes of analysis, maintenance, or transport. This may also allow different types of filter housings and filter traps to be used with apparatus 10 depending on the particular environmental monitoring required (e.g. depending on the particular contaminants being modelled or evaluated).

When multiple filter traps, such as filter traps 20 and 22, are used, they can each be fluidly coupled to the fluid flowpath at a position downstream from the flow-through detectors. In some examples, second filter trap 22 may be fluidly connected in series downstream from first filter trap 20, for instance using fluid coupling 28 (FIG. 1B). The first filter trap 20 may have a first filter trap outlet 44, while the second filter trap 22 has a second filter trap outlet 46 (FIG. 5). Each of the first filter trap outlet 44 and the second filter trap outlet 46 can be fluidly connected to apparatus fluid outlet 32 to allow the stream of fluid to be released after passing through at least one of the filter traps 20, 22.

Alternatively, in some other examples, the first and second filter traps 20, 22 can be fluidly connected in parallel. This may allow the filter housing 14 for one of the first filter trap 20 and the second filter trap 22 to be detached from primary housing 12 without interrupting the fluid communication between the other fluid housing 14 and primary housing 12.

Referring again to FIGS. 1A and 1B, in the illustrated example the primary housing 12 is mounted on a portable chassis 38, and the filter housings 14 are mounted to the primary housing 12. The chassis 38 is configured as a trailer and includes two wheels to 16 rollingly supporting the portable detection apparatus 10. Chassis 38 may also include a coupling 18, such as a hitch for connecting the portable detection apparatus 10 to a vehicle. For instance, chassis 38 may be a road-licensed one-axle trailer that can be towed behind a vehicle such as a car, truck or all-terrain vehicle. This may allow apparatus 10 to be easily moved between sampling locations as desired. Once apparatus 10 has reached its desired location for environmental monitoring, stands 54 can be used to maintain apparatus 10 in an upright position after chassis 38 is detached from the vehicle. In other embodiments the chassis may have a different configuration (more wheels, different dimensions, etc.).

In the illustrated example, the detection apparatus 10 includes a meteorological station or weather sensing unit 74 that is positioned on the top of an extendable or telescoping pole 52. Pole 52 can be extended so that sensing unit 74 is positioned at a greater height when in operation to more accurately obtain meteorological measurements. Sensing unit 74 may include multiple meteorological sensors and an integrated global navigation satellite system (GNSS) such as the global positioning system (GPS) so as to obtain a plurality of measurements in both stationary and moving conditions. The meteorological station 74 may also include at least one of a temperature sensor, a pressure sensor, a rain sensor, and a wind speed sensor. The meteorological station 74 may be configured to measure a variety of variables, including apparent wind speed, apparent wind direction, magnetic compass heading, air temperature, relative humidity, dew point temperature, wind chill temperature, barometric pressure, true wind speed, true wind direction, heading relative to true north, true wind chill temperature. This information can be provided to the detection apparatus controller, and may be used to model atmospheric dispersion of one or more contaminants. An atmospheric plume profile model may be used to model the dispersion of the contaminants. The emission data obtained from the flow-through detectors and filter traps of apparatus 10 can then be used to back-calculate the emission rate from the target source.

Optionally, the portable apparatus 10 may have a relatively compact footprint. This may allow the detection apparatus 10 to be driven on roads and may enable it to be deployed in difficult to access locations or within buildings. Optionally, the overall width of the detection apparatus 10 may be selected so that the detection apparatus 10 can pass through a standard, double-door way in a building. This may help facilitate placing the detection apparatus 10 apparatus within buildings. Referring to FIG. 2A, the detection apparatus 10 may have a width 11 in a first direction and a length 13 in a second direction orthogonal to the first direction. The primary housing may have the same width as the detection apparatus 10 (i.e. width 11), and may have a shorter length 15. Preferably, the width 11 is less than about 5 feet, and optionally the length 13 may also be less than about 5 feet. The primary housing 12 may have a width can be less than about 5 feet and the length 15 can be less than about 3 feet.

Referring to FIG. 1A, the height 17 of apparatus 10 may be variable depending on whether telescopic pole 52 is used. For instance, the detection apparatus 10 may have a height 17 of about 175 cm without telescopic pole 52, while the detection apparatus 10 may have a height of about 267 cm when telescopic pole 52 is employed and extended. Providing a telescopic pole 52 may allow the pole 52 to be retracted when the detection apparatus 10 is in transport, and then extended when the detection apparatus 10 reaches the monitoring location. In some examples, primary housing 12 may have an internal compartment size of about 94 cm$^3$, but may be configured to be larger or smaller based on particular equipment selections and/or expected uses of the apparatus 10.

Optionally, the primary housing 12 may also include a heater, an air conditioning unit, heat pump or other suitable climate control mechanism to control the temperature within primary housing 12. This may be helpful in stabilizing the operating conditions for the flow-through detectors such as the gamma spectrometer and the mercury analyzer when apparatus 10 is deployed for sampling. For example, it may be desirable to keep the interior of the apparatus 10 at a different temperature than the surrounding environment. Optionally, when in operation, it may be desirable to erect a temporary shelter, such as a tent or other such shelter, around apparatus 10 to provide shade and potentially reduce the workload for the air conditioner.

Preferably, the apparatus 10 can be configured to have a total weight that is low enough to allow the apparatus 10 to be transported on standard roadways, and optionally so that the apparatus can be moved across unpaved surfaces (such as gravel or dirt roads, off road, etc.) to a desired monitoring location. It may also be preferable in some configurations to configure the apparatus 10 to have a weight that is low enough so that a single user, or possible two or more users, can manually roll the apparatus 10 across a surface without the need for a vehicle or other powered assistance. This may help users maneuver the apparatus 10 into a variety of monitoring locations which may be otherwise inaccessible using larger and/or heavier apparatuses. For example, the total weight of the apparatus 10 may be less than 2000 Kg, and optionally may be less than about 1000 Kg, less than about 750 Kg or less than about 500 Kg. In the illustrated configuration, the total weight of apparatus 10, including the primary housing 12, filter housings 14 and their contents is about 565 kg.

Reference will now be made to FIGS. 2A-2B. FIG. 2A is a perspective view of portable detection apparatus 10 from the top, back and left hand side similar to FIG. 1B, but the walls of primary housing 12 and filter housing lid 24 are shown as being transparent. FIG. 2B is another perspective view of portable detection apparatus 10 from the bottom, left and front where again the walls of primary housing 12 are shown as being transparent.

Figure 4A:
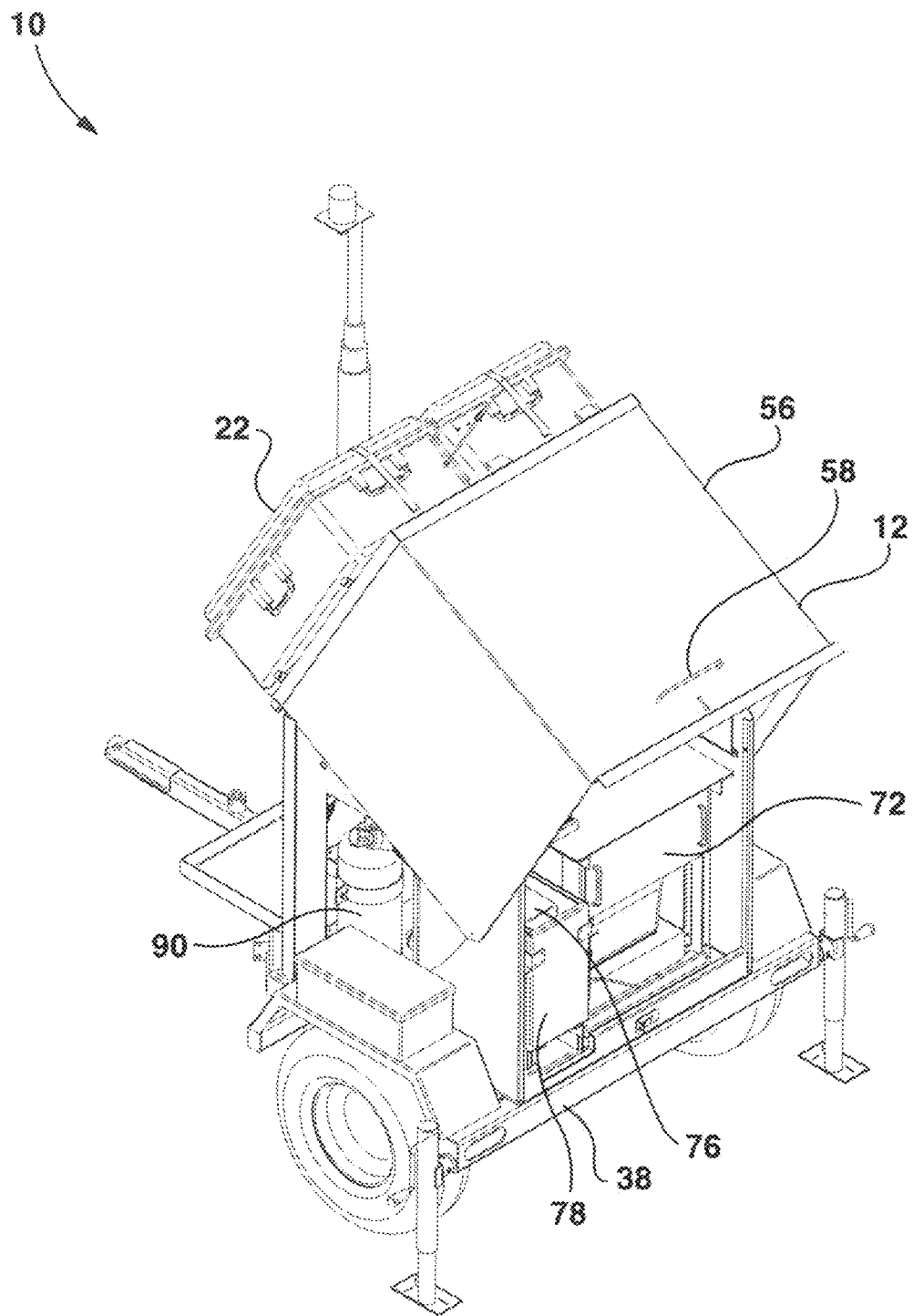
FIG. 4A is a perspective view of one example of the portable detection apparatus of FIG. 1 with the door of the primary housing open.
Figure 4B:
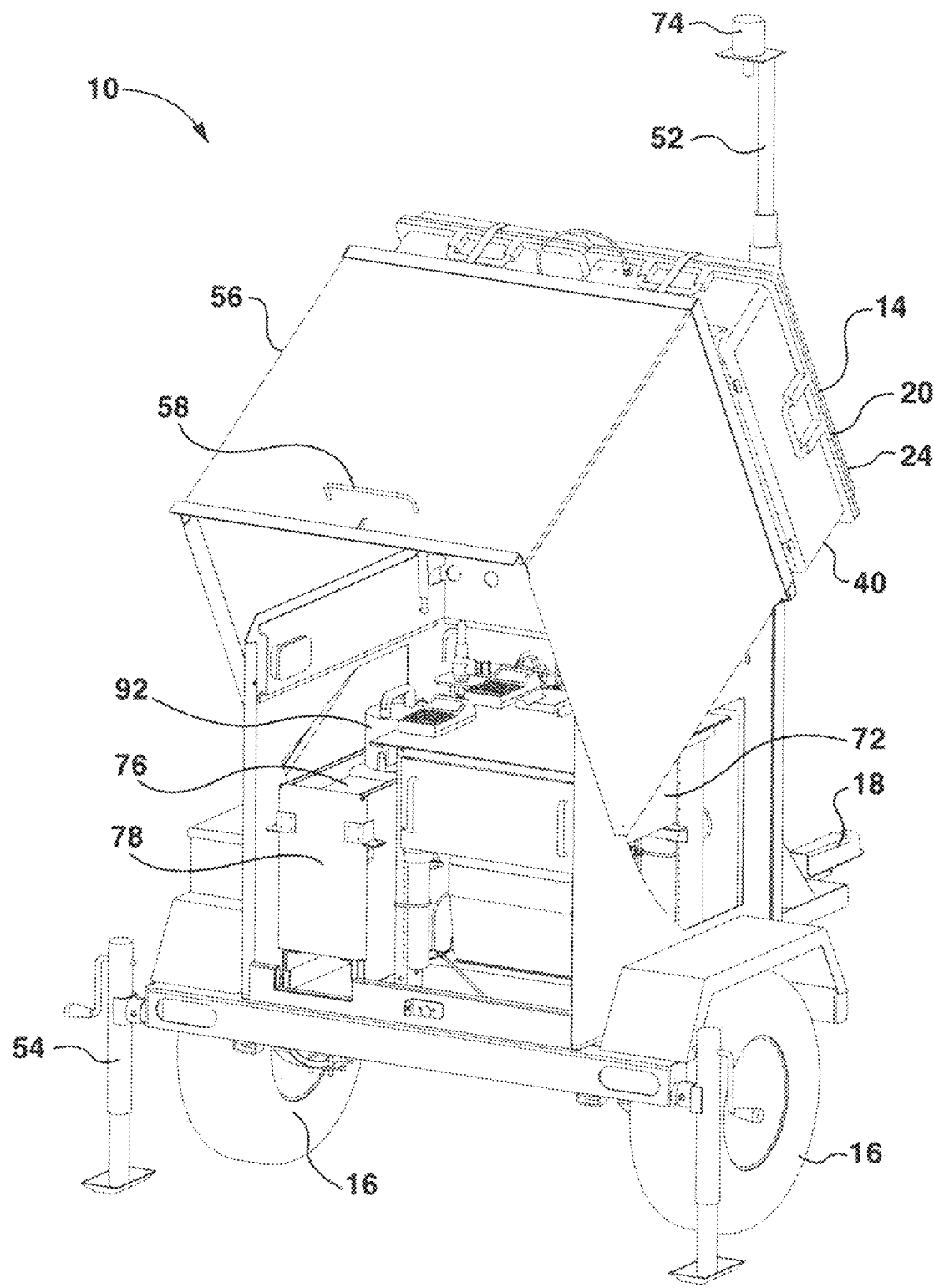
FIG. 4B is another perspective view of one example of the portable detection apparatus of FIG. 1 with the door of the primary housing open.

Primary housing 12 may also include a door 56. Door 56 may be movable between a closed position (FIGS. 1A and 1B) and an open position (an example of which is shown in FIGS. 4A-4B. In the closed position, primary housing 12 may be fluidly sealed with the exception of apparatus fluid inlet 30 and primary housing fluid outlet 36. In the open position, at least one of gamma spectrometer 76 and mercury analyzer 72 may be accessible. This may provide access for maintenance, or calibration, or other adjustments to gamma spectrometer 76 and/or mercury analyzer 72.

Reference will now be made to FIGS. 4A-4B, shown therein is portable detection apparatus 10 with the door 56 of primary housing 12 in the open position. FIG. 4A shows a perspective view from the back, left and top, while FIG. 4B shows a perspective view from the back, right and top.

With the door 56 in the open position, an operator can access gamma spectrometer 76 and mercury analyzer 72, as well as other components contained within primary housing 12. For instance, primary housing 12 generally includes at least one controller or processor that regulates and controls the operation of the components such as gamma spectrometer 76, mercury analyzer 72 and filter traps 20, 22. For instance, the controller may control the operation of the valve assemblies in filter traps 20, 22.

Door 56 may include a handle 58 to allow an operator to easily transition door 56 between the open position and the closed position. In some cases, door 56 may also include a lock to secure apparatus 10 in the closed position. This may provide some security for apparatus 10 when left unattended at a sampling location.

As shown in FIG. 2, in the illustrated example the primary housing 12 houses gamma spectrometer 76 and mercury analyzer 72. In some examples, the apparatus 10 may include a pump or other suitable apparatus for circulating fluid through the fluid flowpath. In the illustrated example, is an integral component of the TEKRAN mercury analyzer 72. The pump may be integral with mercury analyzer 72. In other cases, a separate pump may be used to circulate the fluid through the fluid flowpath.

Primary housing 12 may also include a gas supply container 90. Container 90 may contain an inert gas such as argon for use as a carrier fluid by mercury analyzer 72. Mercury analyzer 72 may require a substantially constant, or regulated, flow of gas. Accordingly, a regulator 62 may be fluidly connected between container 90 and mercury analyzer 72 to control the flow of carrier gas therebetween.

In some cases, primary housing fluid outlet 36 may also include relief outlets 50 and 68. Relief valve outlets 50 and 68 may be used to vent fluid from the fluid flowpath in the event of malfunctions along the fluid flowpath or sample line. Relief outlets 50 and 68 may be fluidly coupled to pressure relief valves operable to vent fluid in the event of a pressure build-up.

Figure 3A:
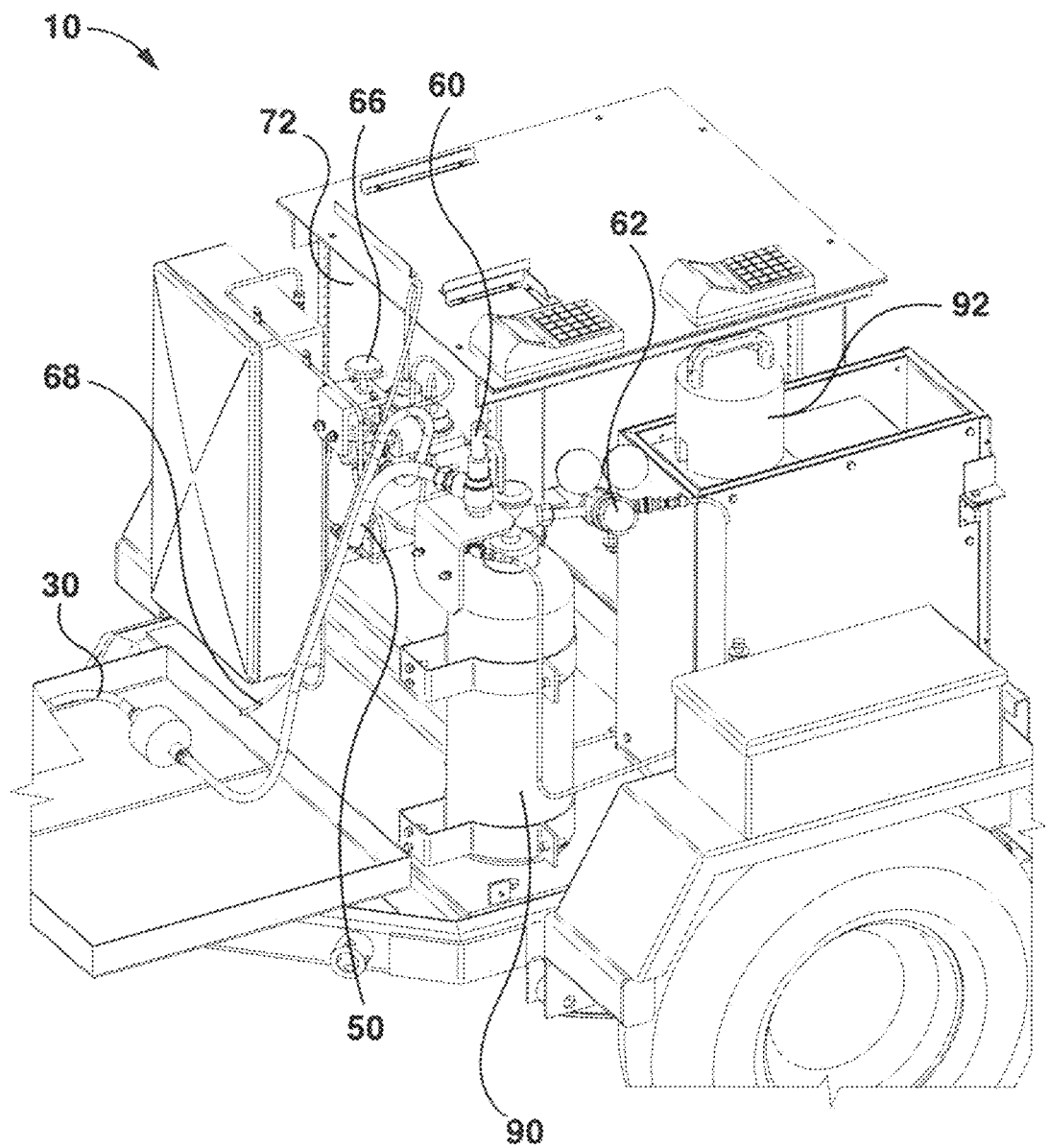
FIG. 3A is a perspective view of one example of the portable detection apparatus of FIG. 1 with the primary housing removed.
Figure 3B:
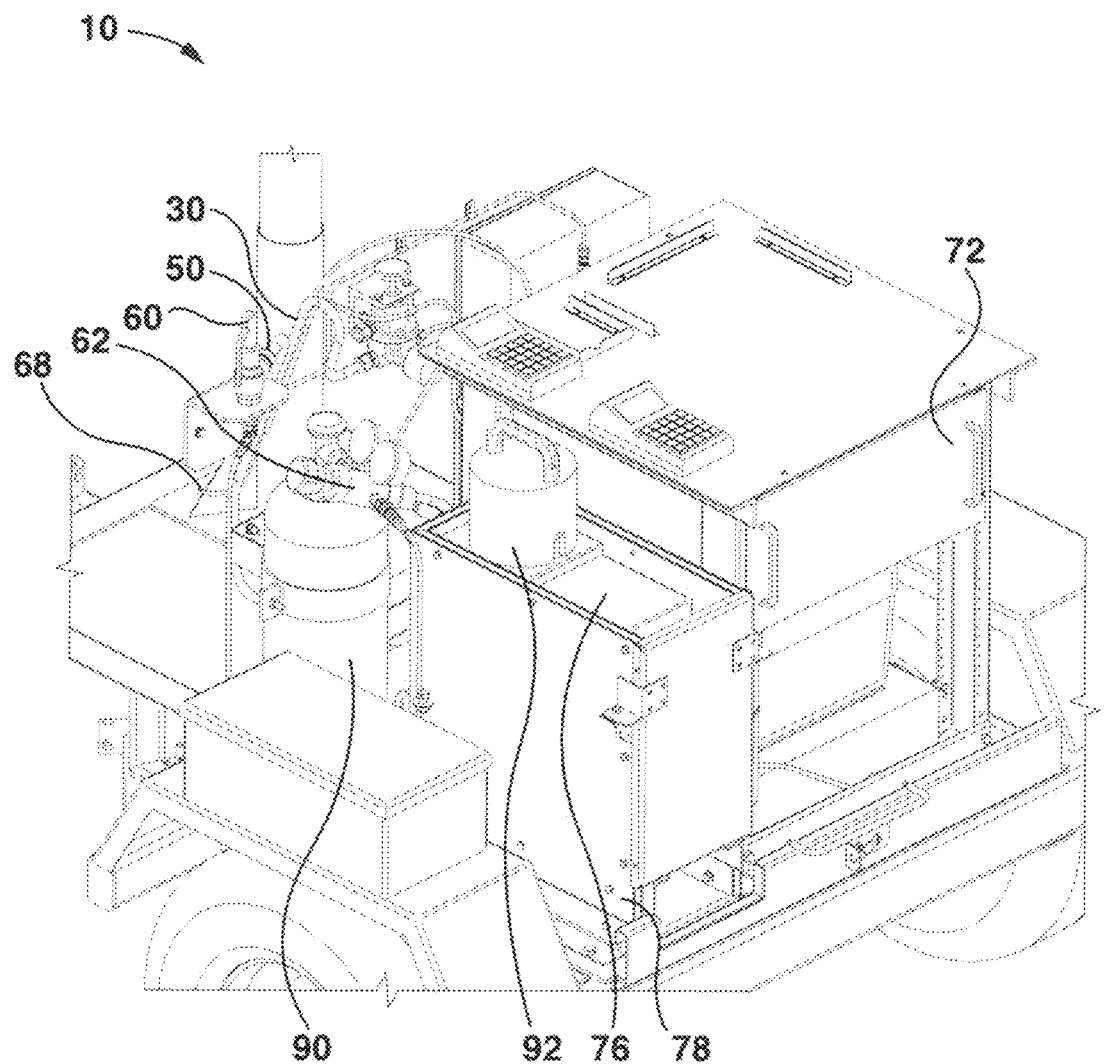
FIG. 3B is another perspective view of one example of the portable detection apparatus of FIG. 1 with the primary housing removed.
Figure 3C:
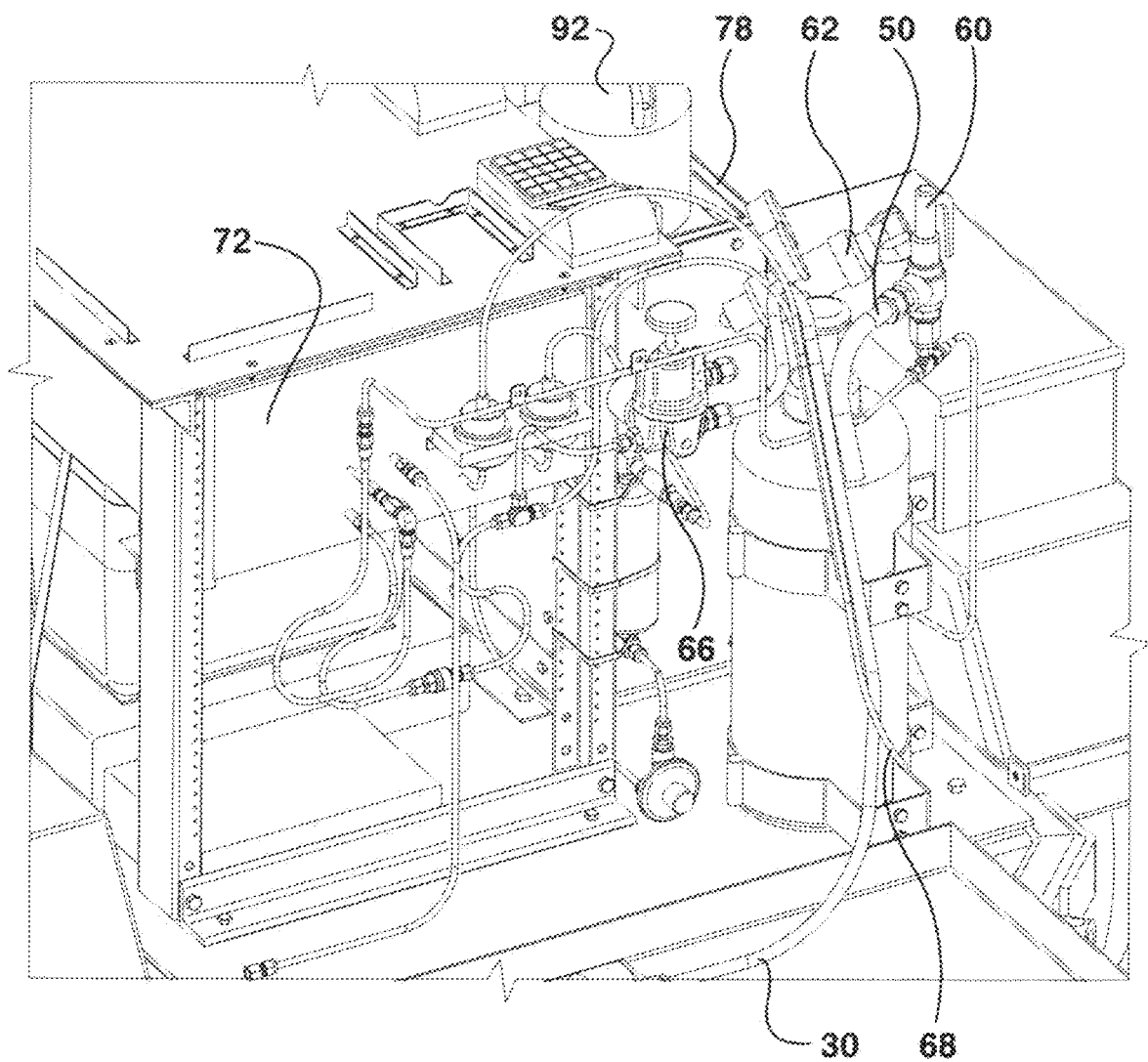
FIG. 3C is a zoomed in perspective view of a portion of one example of the portable detection apparatus of FIG. 1 with the primary housing removed.

Reference will now be made to FIGS. 3A-3C, in which the detection apparatus 10 is shown with the primary housing 12 and filter traps 14 removed to reveal the underlying portions of the apparatus 10. FIG. 3A shows a perspective view from the front, left and top while FIG. 3B shows a perspective view from the back, left and top. FIG. 3C shows a zoomed in perspective view of a portion of portable detection apparatus 10 from the front, right and top.

FIGS. 3A-3C illustrate example components of portable detection apparatus 10 with primary housing 12 and filter housings 14 removed. Apparatus fluid inlet 30 acquires a stream of fluid into the fluid conduit or sampling line. The fluid conduit enters apparatus 10 and runs over gamma spectrometer 76, which is positioned to engage the fluid flowpath or sample line. Gamma spectrometer 76 is operable to detect radiation or ionizing radiation emitted by the fluid while the fluid is flowing through the fluid flowpath.

The fluid conduit may be held on the top of gamma spectrometer 76 by a containment device that includes at least one sample channel (i.e. containment geometry) to receive a portion of the fluid conduit/sample line. Securing the sample line within the sample channel may help secure the sample line in the preferred location for measurements. Optionally, more than one sample channel may be provided for use with the gamma spectrometer 76. The sample channels may be interchangeable, and each sample channel may be configured to receive a specific size or type of sample line, or other conduit. For example, the gamma spectrometer 76 may also include a second sample channel. The second sample channel may be a different size from the first sample channel and may receive a portion of a second fluid conduit that has a different size than the fluid conduit received by the first sample channel.

Figure 8:
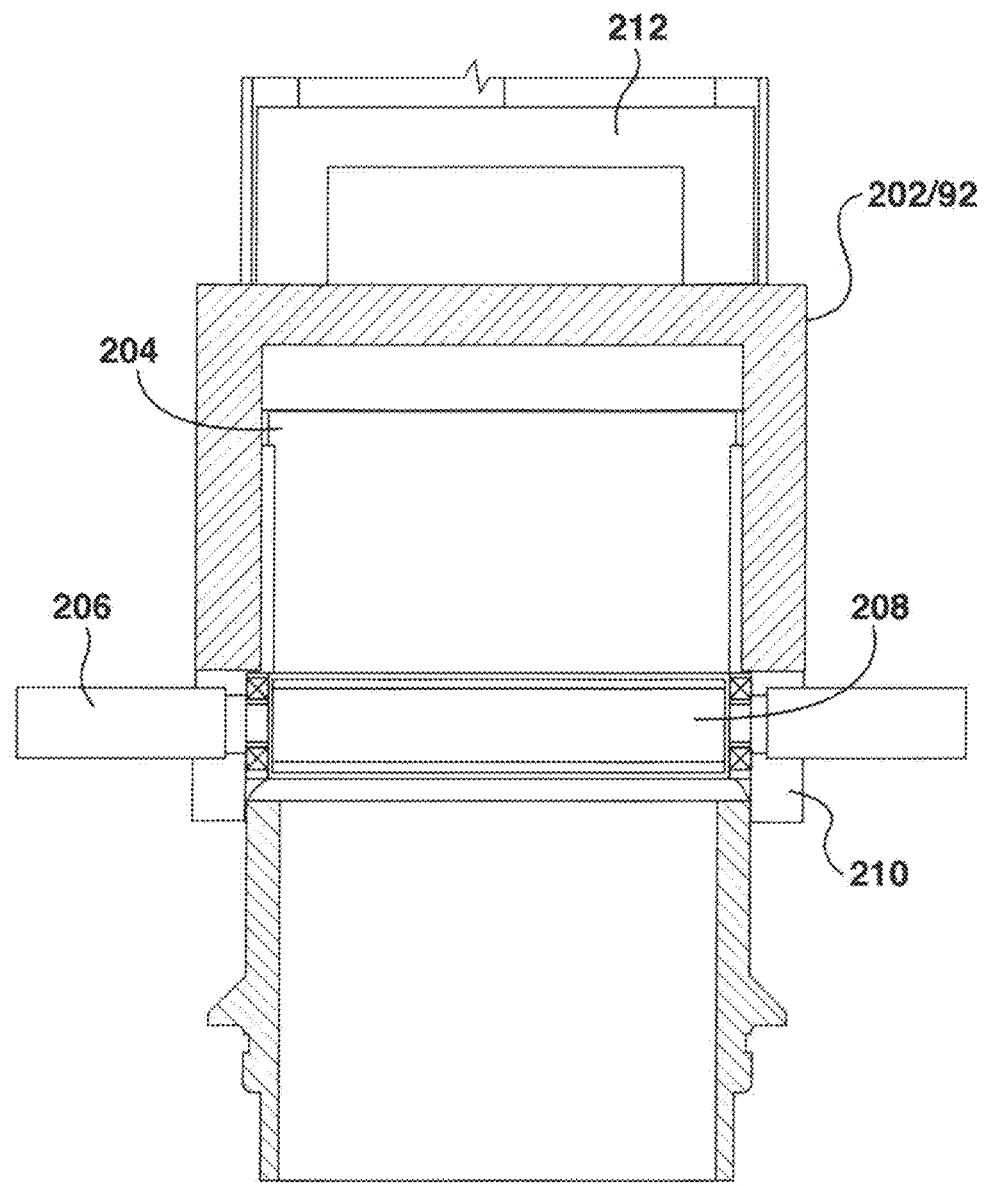
FIG. 8 is a cross-section of an example of a radiation shield for a gamma spectrometer that may be used with the portable detection apparatus of FIG. 1.

Gamma spectrometer 76 may be operable to detect ionizing radiation emitted by the fluid while the fluid is flowing through the first sample channel. In some examples, apparatus 10 may also include a radiation shield 92 at least partially covering or surrounding the gamma spectrometer 76, the sample channel and the portion of the fluid conduit received within the sample channel from background radiation. This may help reduce background radiation levels in the sample channel and may help facilitate obtaining real-time radiation measurements on a flowing fluid. An example of radiation shield is shown in FIG. 8. In some cases, the radiation shielding around gamma spectrometer 76 may also include additional radiation shield 78.

Gamma spectrometer 76 may be configured to continuously sample the fluid flowing through the fluid conduit. Gamma spectrometer may continuously identify and quantity radionuclides passing through the fluid flowpath or sampling line. Generally, gamma spectrometer 76 may be any variety of instrument that can be used to detect ionizing radiation, such as gamma radiation. For example, a portable high purity germanium based radionuclide identifier may be used. The gamma spectrometer may have an energy range from 20 KeV to 2.0 MeV. In some cases, gamma spectrometer 76 may also include at least one battery.

Gamma spectrometer 76 is generally configured to identify radiological isotopes present in the fluid. In some examples, gamma spectrometer 76 may also include a dose rate monitoring device configured to monitor the dose rate of the ionizing radiation in the fluid. For example, the dose rate monitoring device may be a Geiger-Müller tube that allows the dose rate to be continuously monitored.

Gamma spectrometer 76 may be configured to communicate with a controller contained within primary housing 12. Optionally, or in addition, the gamma spectrometer 76 may include a wireless communication module to allow wireless communication with the controller or any other computer device with wireless range. In some cases, apparatus 10 may also include an additional gamma dose rate meter. The additional gamma dose rate meter may be used to continuously monitor the background radiation for the gamma spectrometer 76. The additional gamma dose rate meter may also be used to optimize the position of trailer during sampling.

Typically during operation of the apparatus 10 the gamma spectrometer 76 is not directly exposed to the fluid flow, or the contaminants therein. This may help reduce the chance of gamma spectrometer 76 becoming contaminated during active sampling.

Mercury analyzer 72 may also be provided in the fluid flowpath to engage the sampling line and analyze the fluid flowing through the fluid flowpath. In some cases, the gamma spectrometer 76 is upstream from the mercury analyzer 72. In such cases, after the fluid has passed through the portion of the fluid flowpath sampled by gamma spectrometer 76, the fluid will then pass to mercury analyzer 72. The fluid may enter a sample air inlet of mercury analyzer 72. Alternatively, the mercury analyzer 72 may be upstream from the gamma spectrometer 76.

In some examples, mercury analyzer 72 may be configured for radioactive sampling. In other examples, mercury analyzer 72 may be configured for non-active sampling. Mercury analyzer 72 may also be communicatively coupled to the controller housed within primary housing 12, or other suitable controller. This may allow the sample collection period for mercury analyzer 72 to be adjusted as desired. For example, mercury analyzer 72 may employ 2.5 or 5 minute sample collection periods, where 1 litre per minute of fluid is sampled. In some cases, mercury analyzer 72 may have a detection limit of 0.01 hg/m$^3$. After the fluid exits mercury analyzer 72 it may pass through fluid conduit outlet 36 to filter housing inlet 42, where contaminants may be trapped using filter traps such as filter traps 20 and 22.

In some cases, mercury analyzer 72 may include an integral pump. The pump may be used to circulate fluid through the fluid flowpath of apparatus 10. Mercury analyzer 72 may have a pump exhaust port, which may operate as the fluid conduit outlet 36. In the illustrated example, the integral pump within the mercury analyzer 72 is the only pump used to move fluid through the sample line. In other examples, additional pumps may be provided in addition to, or in place of, the pump within the mercury analyzer 72.

Portable detection apparatus 10 may be modular. As a result, in some examples, portable detection apparatus 10 may also include additional sensors as required. For example, one or more gas monitors may be included in apparatus 10 for personal, area, or remote sensing. The gas monitors may be configured to monitor levels of combustible gases such as $CH_4$, $CO_2$, CO, $H_2S$, $SO_2$, NO, $H_2$, and $O_2$ for example. Additional sensors may also include a high-volume continuous air sampler for suspended particulate measurements.

The additional sensors may include a plurality of sensors related to meteorological conditions such as wireless temperature, humidity, and barometric pressure probe and UVA/UVC sensors. The additional sensors may further include a dynamic flux chamber to measure evasion or volatilization from ground or surface water.

Apparatus 10 may also include a flow meter coupled to the fluid flowpath or sample line. The flow meter can be used to calibrate the flow-rate through the fluid flowpath.

Apparatus 10 may also include at least one on board power source electrically connected to the gamma spectrometer 76, mercury analyzer 72 and filter traps 20, 22, and/or any of the other onboard equipment. In some examples, apparatus 10 may include a standalone power source such as one or more batteries or a generator (e.g. a gasoline generator such as a Honda 3000™ generator) for remote applications.

Apparatus 10 may also include pressure relief valves to help protect apparatus 10 from over-pressure situations. A first pressure relief valve 60 may be located in the fluid flowpath after gas cylinder 90. The first pressure relief valve 60 may discharge if there is an over-pressure between gas cylinder 90 and mercury analyzer 72. First pressure relief valve 60 may be fluidly connected to first relief outlet 50 to allow the fluid to be discharged into the atmosphere, external to primary housing 12.

A second pressure relief valve may be located between mercury analyzer 72 and filter housings 14. The second pressure relief valve may be configured to release if one of the valves in the valve assembly of filter housings 14 fails.

Primary housing 12 also generally includes at least one storage medium coupled to the controller. The controller may receive data or such as measurements or status information from gamma spectrometer 76, mercury analyzer 72, filter traps 20, 22 and/or sensing unit 74. Such data can then be stored in the storage medium for later analysis or retrieval. For example, the controller may store the mercury concentration of the fluid detected by mercury analyzer 72, the isotope and dose data detected by gamma spectrometer 76 and the current filter 80 that is being sampled in filter traps 20 and 22.

Figure 6B:
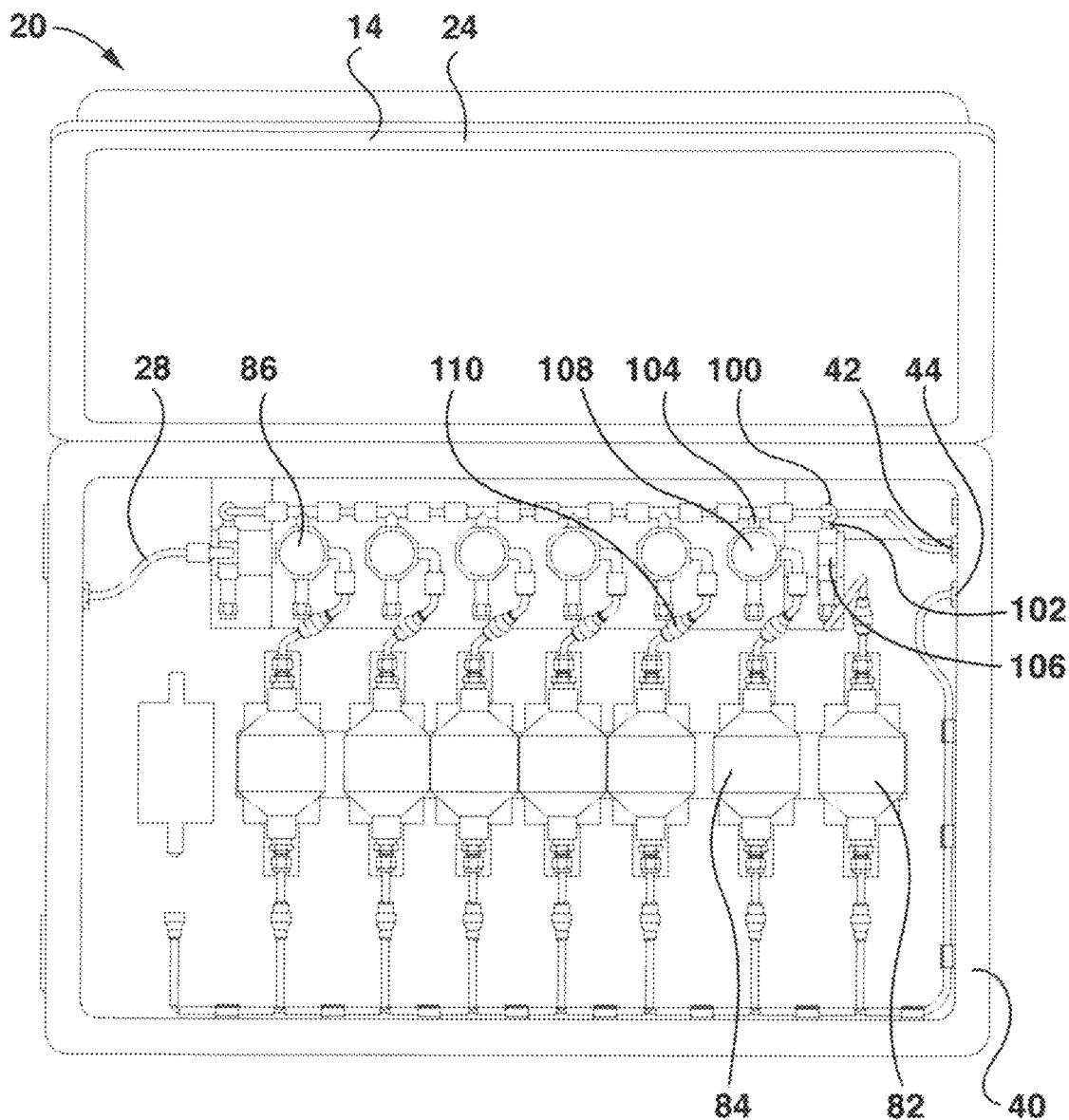
FIG. 6B is a top view of the filter trap of FIG. 6A with the lid open.

Referring to FIGS. 5, 6A-6B the portable detection apparatus 10 preferably includes at least one filter trap, such as first filter trap 20. First filter trap 20 includes a plurality of filters 80 including at least a first filter 82 and a second filter 84. First filter 82 and second filter 84 can be used for collecting gaseous constituents from the acquired stream of fluid.

The filters 80 (including filters 82 and 84) may be any suitable filter that is capable of trapping a desired and/or suspected contaminant. The first filter trap 20 also includes a first valve assembly 86. Each filter 80 including first filter 82 and second filter 84 can be removably connected to first valve assembly 86. First valve assembly 86 may control the flow of the acquired fluid stream through first filter trap 20.

Apparatus 10 may also include or more additional filter traps, which can be connected in series and/or in parallel with each other in the airflow path. In the illustrated example, the apparatus includes a second filter trap 22 in addition to the first filter trap 20. In the illustrated example, the second filter trap 22 is fluidly connected in series with, and downstream of, first filter trap 20. Second filter trap 22 also includes a plurality of filters including at least a third filter 94 and a fourth filter 96. Second filter trap 22 includes a second valve assembly 88 for controlling the flow of the acquired fluid stream through the second filter trap, and distributing the flow of fluid through the filters. Further details of the configuration and operation of the filter traps, filters and valve assemblies will be discussed below with reference to FIGS. 5, 6A-6B.

FIG. 5 shows a top view of portable detection apparatus 10 with the lids 24 removed from filter traps 14. FIGS. 6A-6B show examples of the first filter trap 20. FIG. 6A shows a perspective view of first filter trap 20, while FIG. 6B shows a top view of filter trap 20.

The filter traps provided with examples of portable detection apparatus 10 can be configured to capture contaminants in the fluid acquired using fluid inlet 30. The filter traps are positioned downstream of the flow-through detectors of apparatus 10 so that the capture of contaminants does not affect the measurements performed by the flow-through detectors. Each filter trap includes a plurality of filters 80. Each filter can be used to collect gaseous constituents from the acquired stream of fluid.

Filter housing inlet 42 can be fluidly connected to primary housing or conduit outlet 36. The fluid connection may be made using detachable fluid connector 98. This allows the filter traps to be detached from primary housing 12 if desired. Filter housing inlet 42 is fluidly connected to first filter trap 20.

First filter trap 20 includes a first valve assembly 86 and at least a first filter 82 and a second filter 84. Each filter in first filter trap 20 is removably connected to first valve assembly 86. The path taken by the stream of fluid through first filter trap 20 can be controlled by adjusting the configuration of first valve assembly 86. First valve assembly 86 may be configurable in a first configuration, in which the first filter 82 is fluidly connected to the fluid flowpath and the second filter 84 is fluidly isolated from the fluid flowpath, and a second configuration, in which the second filter 84 is fluidly connected to the fluid flowpath and the first filter 82 is fluidly isolated from the fluid flowpath. In either configuration, the stream of fluid passes through the filter 80 that is fluidly connected to the fluid flowpath and out first filter trap outlet 44.

First valve assembly 86 may be a manifold valve assembly. First valve assembly 86 may have a first manifold inlet 100 connectable in fluid communication with filter housing fluid inlet 42. First valve assembly 86 may also include a first manifold outlet 102 having a first valve 106 and a second manifold outlet 104 having a second valve 108. First valve assembly may include a plurality of additional manifold outlets and corresponding valves, such as the eight manifold valve assembly 86 shown here. First filter 82 may be removably connectable to first manifold outlet 102 and second filer 84 may be removably connectable to second manifold outlet 104. Each of the first valve 106 and second valve 108 may be operable independently.

Second filter trap 22 includes a second valve assembly 88 and at least a third filter 94 and a fourth filter 96. Each filter in second filter trap 2 is removably connected to second valve assembly 88. The path taken by the stream of fluid through second filter trap 22 can be controlled by adjusting the configuration of second valve assembly 88. Second valve assembly 88 may be configurable in a first configuration, in which the third filter 94 is fluidly connected to the fluid flowpath and the fourth filter 96 is fluidly isolated from the fluid flowpath, and a second configuration, in which the fourth filter 96 is fluidly connected to the fluid flowpath and the third filter 94 is fluidly isolated from the fluid flowpath. In some examples, second valve assembly 88 may be generally of the same construction as first valve assembly 86.

Each of first filter trap 22 and second filter trap 22 may be communicatively coupled to the controller container in primary housing 12. The controller may control the configuration of first valve assembly 86 and second valve assembly 88 to control which filter 80 is currently capturing gaseous constituents from the stream of fluid. The controller may operate each of the valves in first valve assembly 86 and second valve assembly 88 independently of each other.

The controller may adjust the valve positions for first valve assembly 86 and second valve assembly 88 so that only a single filter sampling the fluid stream at a single time. Each filter 80 may be used to sample the fluid for a specific time period, such as four hours for example. After the time period has elapsed, the valve positions may be adjusted so that a subsequent filter 80 samples the fluid stream. As such, analysis of the filters 80 may indicate changes in the gaseous constituents in a time-lapsed manner.

As mentioned above, each filter 80 is removably connected to the valve assemble of the corresponding filter trap. This allows the filters to be easily removed after sampling is complete and for new filters to be inserted as desired. Once sampling is complete, a filter 80 can be removed from filter housing 14 using quick disconnect fittings 110. The filter 80 can then be sent for regeneration and analysis.

The filter traps can be installed in parallel and the valve assemblies of the filter traps can be controlled by the controller to provide a continuous single path for the sampled air. The valve position of each valve in the filter traps can be recorded alongside the data received from the detectors such as mercury analyzer 72 and gamma spectrometer 76. Thus, when the filters 80 are later analyzed the analysis can be correlated with the measurements acquired contemporaneously by apparatus 10. The collection time for each filter 80 can also be controlled by the controller either based on pre-set durations set by an operator, or in response to changes in emission rates as detected by other sensors in apparatus 10.

In some examples, the filters 80 may be TEDA (TriEthyleneDiAmine) impregnated activated charcoal filter cartridges for Iodine-131 collection. Alternative filters, such as Carbon-14 and Tritium filters may also be used in other examples of apparatus 10. In different examples, filters 80 may be housed within aluminum inline filter holders or stainless steel cylinders. For example, the carbon-14 or tritium filters may be housed in stainless steel cylinders, while the Iodine-133 filters may be housed in aluminum filter holders.

While tritium filters and carbon-14 filter may use similar housings, the filter material may be different. Tritium filters may include molecular sieve (MS) 3 Å beads, while the carbon-14 traps may contain molecular sieve 4 Å. In some cases, the tritium and carbon-14 filters may be sampled in sequence. As the filter materials are different, placing the tritium filters before the carbon-14 filters may not affect the collection of carbon-14 due to the different filter materials used. As a result, in some examples tritium filters could be employed in first filter trap 20, while carbon-14 filters are employed in second filter trap 22.

Figure 7:
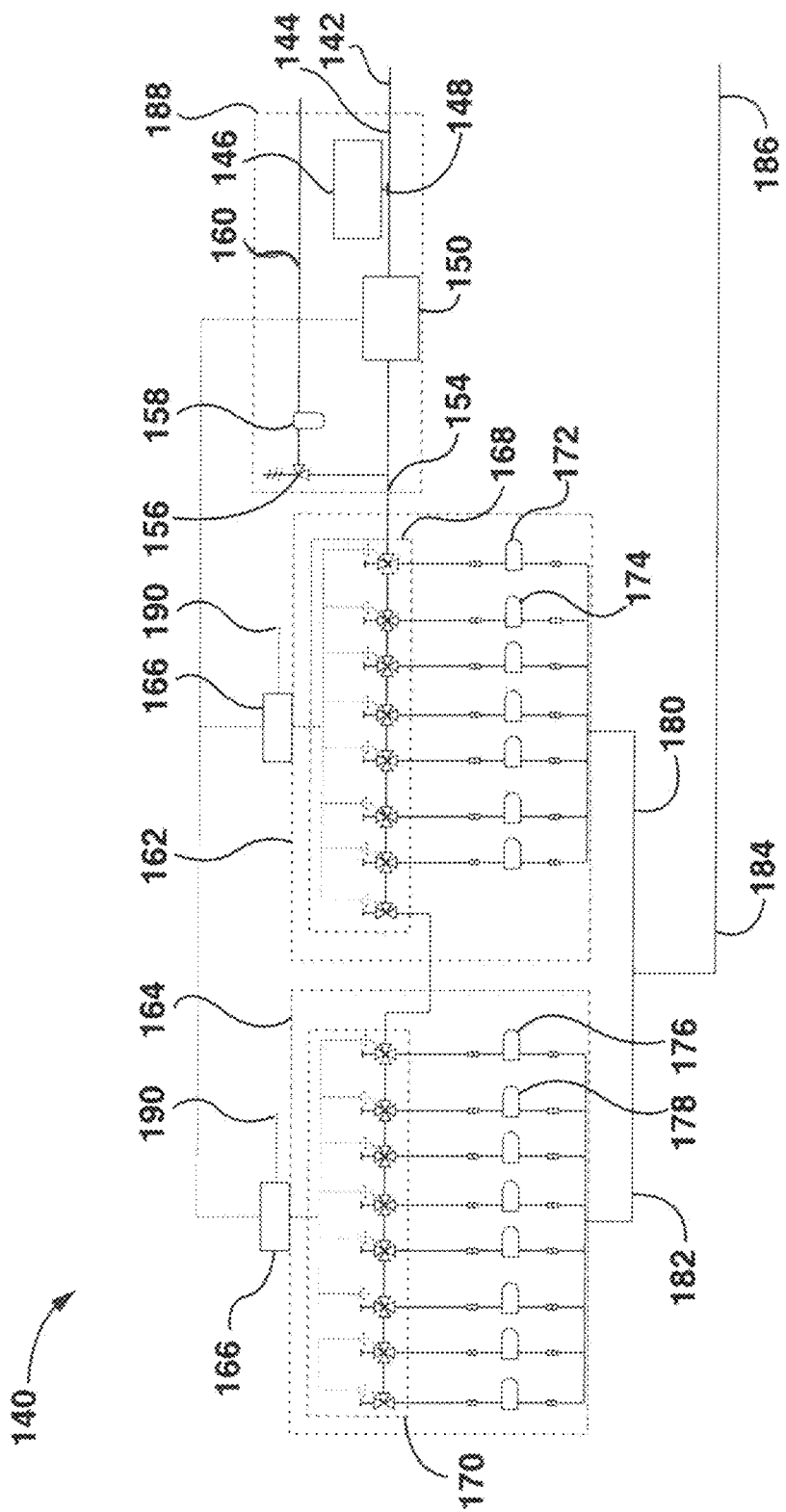
FIG. 7 is a block diagram of one example of a portable detection apparatus.

Referring now to FIG. 7, shown therein is a schematic diagram of a portable detection apparatus 140. The schematic diagram illustrates the fluid flowpath or sample line traversed by a fluid in portable detection apparatus 140. Portable detection apparatus 140 may be an example of portable monitoring apparatus 10.

Apparatus 140 includes an apparatus inlet 142. Apparatus inlet 142 is a fluid inlet used to draw a stream of fluid into apparatus 140. Apparatus inlet 142 is fluidly connected to a fluid conduit 144. Fluid conduit 144 may be contained within a primary housing 188.

Fluid conduit 144 passes by, and is engaged by, gamma spectrometer 146. Gamma spectrometer 146 may include at least one sample channel 148 that is sized to removably receive a portion of fluid conduit 144. Gamma spectrometer 146 may be used to detect radiation in stream of fluid passing through fluid conduit 144 as described above. In general, gamma spectrometer 146 may be similar to gamma spectrometer 76 described above.

After passing through sample channel 148, fluid conduit 144 may enter mercury analyzer 150. Mercury analyzer 150 may also analyze the fluid passing through fluid conduit 144. Mercury analyzer 150 may be generally similar to mercury analyzer 72 described above.

After passing through mercury analyzer 150, the fluid flowpath may exit primary housing 188 at fluid conduit outlet 154. After exiting primary housing 188, the fluid flowpath may be fluidly connected to first filter trap 162. Primary housing 188 may also include a relief valve 156 fluidly connected to fluid conduit 144. Relief valve 156 may be configured to relief an over-pressure situation by discharge the fluid from fluid conduit 144 using relief outlet 160. For example, if a valve assembly of first filter trap 162 fails an over-pressure situation may arise, and relief valve 156 may discharge. A filter 158 may be used to filter contaminants from the fluid discharged by relief valve 156.

First filter trap 162 includes a first valve assembly 168 and at least a first filter 172 and a second filter 174. First filter trap 162 may be generally similar in construction and operation to first filter trap 20 described above. First valve assembly 168 is coupled to a controller 166. Controller 166 may control the operation of first valve assembly 168, thereby controlling the path of the fluid through apparatus 140. Controller 166 may be coupled to power source 190. In some examples, controllers 166 and power sources 190 may be contained within primary housing 12/188 (not shown). First filter trap 162 has a first filter trap outlet 180.

First filter trap 162 is connected in series with second filter trap 164. Second filter trap 164 includes a second valve assembly 170 and at least a third filter 176 and a fourth filter 178. Second filter trap 164 may be generally similar in construction and operation to second filter trap 22 described above. Again, second filter trap 164 is coupled to controller 166 which may control the operation of second valve assembly 170. Second filter trap 164 has a second filter trap outlet 182.

Second filter trap outlet 182 and first filter trap outlet 180 are both fluidly connected to filter housing outlet 184. Filter housing outlet 184 is in term fluidly connected to apparatus fluid outlet 186. When the stream of fluid passes through primary housing 188, the stream passes through at least one of the filters in the first filter trap 162 or the second filter trap 164, and then out the corresponding filter trap outlet to filter housing outlet 184 and then to apparatus fluid outlet 186 where it is discharged.

In some examples (not shown), the stream of fluid may pass through one filter in the first filter trap 162 and then another filter in the second filter trap 164. This may occur when the first filter trap 162 employs a different filter type from the second filter trap 164. For example, first filter trap 162 may employ tritium filters such as those mentioned above, and second filter trap 164 may employ carbon-14 filters. Placing the tritium filters before the carbon-14 filters may not affect the collection of carbon-14 due to the different filter materials used.

Referring now to FIG. 8, shown therein is a cross-section of a radiation shield 202 that may be used in some examples of portable detection apparatus 10. Radiation shield 202 may be an example of radiation shield 92 discussed above.

In the illustrated example the radiation shield 202 is configured to rest on top of a gamma spectrometer such as gamma spectrometer 76. Radiation shield 202 may be an iron shield to shield the gamma spectrometer and sampling line from gamma and x-ray radiation and improve the detection limit of gamma spectrometer. In some examples, radiation shield 202 may have a thickness of greater than 1.2 cm. Radiation shield 202 may have a half value layer (HVL) for gamma and x-ray radiations of 1.170 cm. In such examples, radiation shield 202 may block half of the energy of 0.55 MeV.

Radiation shield 202 may also be used to secure a sample channel or sampling jar in place while the gamma spectrometer is sampling. Generally, radiation shield 202 may be operated in two configurations (both of which are overlaid in FIG. 8. In a first configuration, radiation shield 202 houses a sampling jar 204. Sampling jar 204 may be used to collect air, soil, sediment, or water. Sampling jar 204 may then be placed under radiation shield 202 to permit in-field measurements by the gamma spectrometer. Radiation shield 202 may hold sampling jar 204 in place on top of the collimator of the gamma spectrometer. Radiation shield 202 may include a handle 212 to permit an operator to remove radiation shield 202 when changing operational configurations.

In a second configuration, radiation shield 202 holds a sample channel 208 in place on top of the collimator of the gamma spectrometer. Radiation shield 202 may include a passage 210 to allow tubing 206 to penetrate into the core of the field without the walls of tubing 206 being compressed. Passage 210 also holds tubing 206 in place during sampling by the gamma spectrometer.

Tubing 206 may be coupled to a sample channel 208. Tubing 206 may enable sample channel 208 to receive a portion of the fluid conduit of the portable detection apparatus. This allows the fluid flowing through the fluid flowpath to be analyzed by the gamma spectrometer. Radiation shield 202 also reduces interference from background radiation during sampling.

Figure 9:
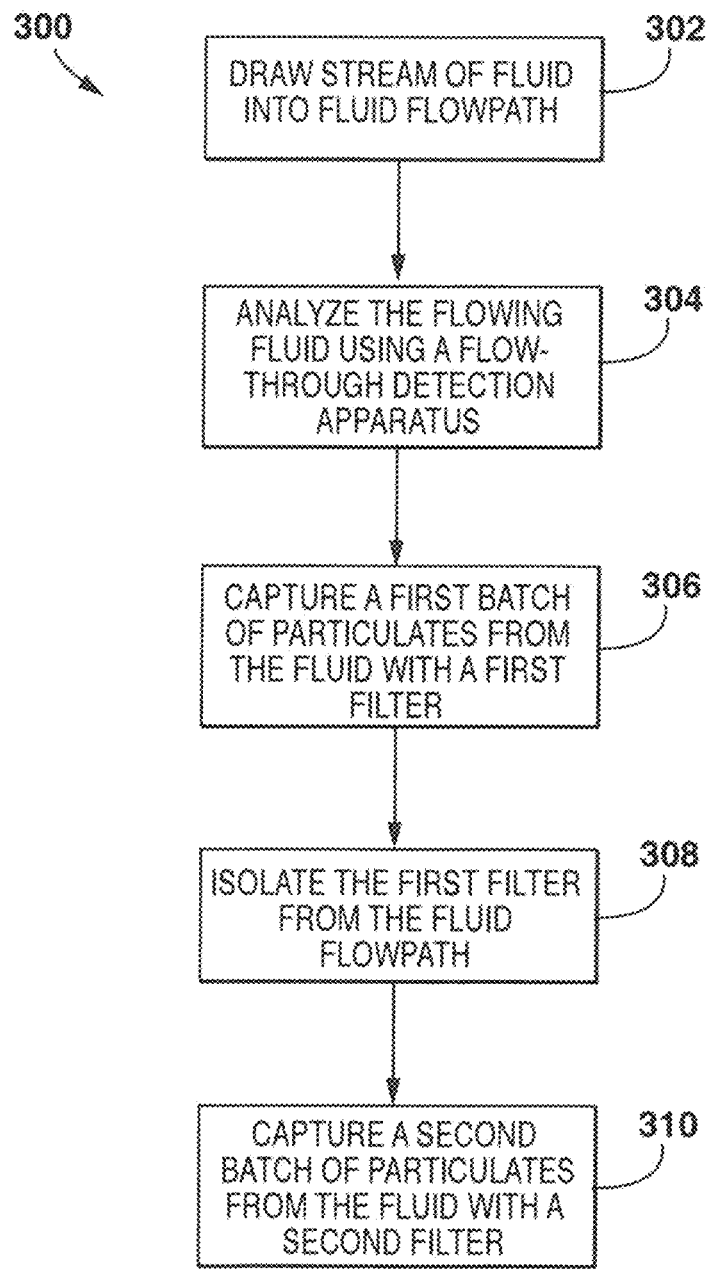
FIG. 9 is a flowchart of one example of a method of monitoring fluid contaminations.

Referring now to FIG. 9, shown therein is an example process 300 for monitoring fluid contaminations. Process 300 is an example process that may be implemented using components of portable detection apparatus 10. Process 300 may also include fewer or greater steps for monitoring fluid contaminations (beyond those shown in FIG. 9) such as those discussed above.

Process 300 begins at 302 by drawing a stream of fluid into a fluid flowpath. For instance, the stream of fluid may be acquired using a sample line such as apparatus fluid inlet 30. In some cases a pump may be used to circulate the fluid within the fluid flowpath. As mentioned above, in some examples the pump may be integral with mercury analyzer 72, while in other examples a separate pump may be used.

At 304, the flowing fluid captured at 302 can be analyzed using a flow-through detection apparatus. The flow-through detection apparatus may be used to detect radiation or mercury levels in the flowing fluid. For example, the detection apparatus may include a gamma spectrometer such as gamma spectrometers 76 and 146 and/or a mercury analyzer such as mercury analyzers 72 and 150. Various other flow-through detectors may also be used, either alone or in combination in the flow-through detection apparatus.

At 306, a first batch of particulates or gaseous constituents can be captured from the fluid using a first filter. The batch may be captured by directing at least a portion of the fluid exiting the flow-through detection apparatus to flow through the first filter. The first filter may be similar to one of the filters 80 mentioned above. The fluid may be directed to flow through the first filter using a valve assembly as discussed above. The valve positions of the valve assembly may be controller by a controller, and the valve positions may be stored over time to ensure that analysis of the filters can be correlated with the analysis performed by the flow-through detection apparatus at 304.

At 308, the first filter can be isolated from the fluid flowpath. The first filter may be isolated by adjusting the valve positions of the valve assembly coupled to the first filter. The first filter may be isolated from the fluid flowpath after it has collected particulates from the fluid for a pre-defined sampling period. In some cases, once the first filter has been isolated from the fluid flowpath, it can be detached from the fluid flowpath to allow for analysis of the captured particulate or to allow a new filter to be used in its place.

At 310, a second batch of particulates can be captures from the fluid with a second filter. The second batch may be captured by directing the at least a portion of the fluid exiting the flow-through detection apparatus to flow through a second filter. Again, the fluid may be directed by adjusting a valve assembly coupled to the second filter.

The second filter may then sample the fluid for a second pre-defined period before it is also isolated from the fluid flowpath. Sampling the fluid using a sequence of filters over different time periods may provide discrete samples of how much particulate was released in each time period. This may allow for changes in the emission rate to be detected. The particulate levels may be provided to the controller for use along with the measurements performed by the flow-through detection apparatus.

Based on the data collected by the controller, a plume profile may be generated. The plume profile dynamically simulates emission plumes based on wind and other environmental conditions. Wind conditions may be measured using a meteorological station such as weather station 74 or other weather stations positioned in the vicinity of the emission source or suspected emission source.

A user may select a date and time for the initial emission. The controller can then identify the relevant meteorological data for the emission. The controller generates a puff model that simulates the release of a series of gaseous spheres. Each sphere represents the amount of material that is issued from the source in a given time period. Each sphere may be generated based on the measurements acquired by apparatus 10. In the plume profile model, each individual sphere responds to the wind direction and speed independently of any other issued spheres. Each sphere dissipates in a Gaussian fashion as it ages, regardless of its position. If the wind changes speed or direction, the spheres respond in kind. Multiple sources may be profiled by duplicating each sphere of the primary source, scaled to the intensity, and displaced from the primary by a known distance.

The controller may generate an activity averaged plume over any time period. This activity averaged plume can be used to determine the concentration of a gaseous constituent at any point in the time period. Once a plume has been generated or modelled, the controller can determine the emission rate from a known or suspected source based on the measured concentration at a sampling point downwind of the source. The emission rate may be determined by setting an arbitrary emission rate. The controller can then generate a modelled concentration at the sampling point based on the plume profile generated. Using a ratio of the modelled concentration (based on the arbitrary/modelled emission rate) to the measured concentration, the actual emission rate at the source can be determined. The ratio may take the form of:

$$\frac{\text{modelled emission rate}}{\text{measured emission rate}} = \frac{\text{modelled concentration}}{\text{measured concentration}}$$

What has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A portable detection apparatus comprising:
   a) an apparatus fluid inlet to draw in a stream of fluid, an apparatus fluid outlet and a fluid flowpath extending therebetween;
   b) a pump for circulating the fluid through the fluid flowpath;
   c) at least one flow-through detection apparatus configured to analyze the fluid as it is flowing through the fluid flowpath; and
   d) at least a first filter trap provided in the fluid flowpath downstream from the at least one flow-through detection apparatus, the first filter trap configured to capture a first batch of particulates from the stream of fluid by directing at least a portion of the fluid exiting the at least one flow-through detection apparatus to flow through a first filter, wherein the first filter trap comprises a first valve assembly and a second filter, the first valve assembly configurable in a first configuration, in which the first filter is fluidly connected to the fluid flowpath and a second configuration in which the first filter is isolated from the fluid flowpath and the second filter is fluidly connected to the fluid flow path to capture a second batch of particulates from the stream of fluid.

2. The apparatus of claim 1, wherein the fluid flowpath comprises a fluid conduit having a conduit inlet and a conduit outlet downstream from the conduit inlet, and at least one flow-through detection apparatus is between the conduit inlet and the conduit outlet and the first filter trap is between the conduit outlet and the apparatus fluid outlet.

3. The apparatus of claim 2, wherein the at least one flow-through detection apparatus comprises a first sample channel that is sized to removably receive a portion of the fluid conduit, and wherein the at least one flow-through detection apparatus is operable to analyze the fluid while the fluid is flowing through the first sample channel.

4. The apparatus of claim 1, wherein the at least one flow-through detection apparatus is configured to detect ionizing radiation emitted by the fluid while the fluid is flowing through the fluid flowpath and further comprising a radiation shield at least partially covering the at least one flow-through detection apparatus and the sample channel to shield the portion of the fluid conduit received within the sample channel from background radiation.

5. The apparatus of claim 1, wherein the first valve assembly comprises a first manifold having a first manifold inlet connectable in fluid communication with the filter housing fluid inlet, a first manifold outlet having a first valve and a second manifold outlet having a second valve, and wherein the first filter is connectable to the first manifold outlet and the second filter is connectable to the second manifold outlet.

6. The apparatus of claim 5, wherein the first valve and second valve are operable independently of each other.

7. The apparatus of claim 1, further comprising at least two wheels rollingly supporting the portable detection apparatus and a coupling for connecting the portable detection apparatus to a vehicle and wherein the portable detection apparatus comprises a width in a first direction and a length in a second direction that is orthogonal to the first direction, and wherein the width and length are each less than about 5 feet.

8. The apparatus of claim 1, a second filter trap in the fluid flowpath downstream from the at least one flow-through detection apparatus, the second filter trap comprising a second valve assembly and at least a third filter and a fourth filter configured for capturing particulates from the stream of fluid and removably connected to the second valve assembly, the second valve assembly configurable in a first configuration, in which the third filter is fluidly connected to the fluid flowpath and the fourth filter is fluidly isolated from the fluid flowpath, and a second configuration, in which the fourth filter is fluidly connected to the fluid flowpath and the third filter is fluidly isolated from the fluid flowpath.

9. The apparatus of claim 8, a primary housing containing the at least one flow-through detection apparatus, a first filter housing containing the first filter trap and a second filter housing containing the second filter trap, wherein the first filter housing and second filter housing are external to the primary housing and are detachably mounted to the primary housing.

10. The apparatus of claim 9, wherein the second filter trap is fluidly connected in parallel with the first filter trap whereby one of the first filter housing and the second filter housing can be detached from the primary housing without interrupting the fluid communication between the other of the first filter housing and the second filter housing and the primary housing.

11. The apparatus of claim 1, further comprising at least one onboard power source electrically connected to at least one flow-through detection apparatus and filter trap.

12. A portable detection apparatus comprising:
   a) an apparatus fluid inlet to draw in a stream of fluid, an apparatus fluid outlet and a fluid flowpath extending therebetween;
   b) a pump for circulating the fluid through the fluid flowpath;
   c) at least one flow-through detection apparatus configured to analyze the fluid as it is flowing through the fluid flowpath;
   d) at least a first filter trap provided in the fluid flowpath downstream from the at least one flow-through detection apparatus, the first filter trap configured to capture a first batch of particulates from the stream of fluid by directing at least a portion of the fluid exiting the at least one flow-through detection apparatus to flow through a first filter;
   e) a primary housing containing the at least one flow-through detection apparatus, and a filter housing that is external the primary housing and contains the first filter trap.

13. The apparatus of claim 12, wherein the apparatus fluid inlet is external and spaced apart from the primary housing by a distance of between about 1 m and 30m.

14. The apparatus of claim 12, wherein the primary housing comprises the apparatus fluid inlet and the filter housing comprises the apparatus fluid outlet and wherein the primary housing comprises a primary housing fluid outlet that forms part of the fluid flowpath and the filter housing comprises a filter housing fluid inlet that forms part of the fluid flowpath and that is detachably fluidly connectable to the primary housing fluid outlet by a fluid coupling.

15. The apparatus of claim 14, wherein the filter housing is detachably mounted to the primary housing and wherein when the filter housing fluid inlet is detached from the primary housing fluid outlet the filter housing is detachable from the primary housing.

16. The apparatus of claim 14, wherein the primary housing has a door that is movable between a closed position, in which the primary housing is fluidly sealed with the exception of the apparatus fluid inlet and the primary housing fluid outlet, and an open position, in which the at least one flow-through detection apparatus is accessible.

17. The apparatus of claim 16, wherein the filter housing has a body and lid that is movable between a closed position and an open position, and wherein the first and second filters are removable when the lid is in the open position, and wherein the lid is movable independently of the door on the primary housing.

18. A portable detection apparatus for detecting a targeted contaminant in the environment, the apparatus comprising:
   a) a sample line configured to receive a flowing fluid from an environment;
   b) a detector positioned to detect a targeted contaminant present in the fluid flowing through the sample line;
   c) a controller linked to the detector and operable to trigger the detector at a predetermined sampling rate while the fluid is flowing through the sample line; and
   d) at least a first filter trap provided in fluid communication downstream from sample line and the detector, the first filter trap configured to capture a first batch of particulates from the stream of fluid by directing at least a portion of the fluid exiting the sample line to flow through a first filter.

* * * * *